United States Patent
Henrichsen et al.

(10) Patent No.: US 9,155,533 B2
(45) Date of Patent: Oct. 13, 2015

(54) SOFT TISSUE DEFECT DEVICE AND ASSOCIATED METHOD

(75) Inventors: Kevin Henrichsen, West Chester, PA (US); Daniel Vennard, West Chester, PA (US)

(73) Assignee: DePuy Synthes Products, Inc., Raynham, MA (US)

( * ) Notice: Subject to any disclaimer, the term of this patent is extended or adjusted under 35 U.S.C. 154(b) by 612 days.

(21) Appl. No.: 13/102,780

(22) Filed: May 6, 2011

(65) Prior Publication Data

US 2011/0276064 A1    Nov. 10, 2011

Related U.S. Application Data

(60) Provisional application No. 61/344,031, filed on May 6, 2010.

(51) Int. Cl.
*A61B 17/04* (2006.01)
*A61B 17/062* (2006.01)

(52) U.S. Cl.
CPC ......... *A61B 17/0469* (2013.01); *A61B 17/0482* (2013.01); *A61B 17/0625* (2013.01)

(58) Field of Classification Search
CPC ........... A61B 17/0469; A61B 17/0491; A61B 17/062; A61B 17/0625; A61B 17/0485; A61B 2017/047; D05B 81/00
USPC ......................................... 606/139, 144–150
See application file for complete search history.

(56) References Cited

U.S. PATENT DOCUMENTS

| | | | |
|---|---|---|---|
| 4,345,601 A | | 8/1982 | Fukuda |
| 5,336,229 A | * | 8/1994 | Noda ............................ 606/144 |
| 5,792,153 A | * | 8/1998 | Swain et al. .................. 606/144 |
| 6,533,796 B1 | * | 3/2003 | Sauer et al. ................... 606/144 |
| 6,551,330 B1 | * | 4/2003 | Bain et al. ..................... 606/144 |
| 6,991,635 B2 | * | 1/2006 | Takamoto et al. ............ 606/144 |
| 6,997,931 B2 | * | 2/2006 | Sauer et al. ................... 606/139 |
| 7,063,710 B2 | * | 6/2006 | Takamoto et al. ............ 606/144 |
| 7,381,210 B2 | | 6/2008 | Zarbatany et al. |
| 7,407,505 B2 | * | 8/2008 | Sauer et al. ................... 606/145 |
| 7,544,199 B2 | * | 6/2009 | Bain et al. ..................... 606/144 |
| 7,744,609 B2 | * | 6/2010 | Allen et al. ................... 606/139 |
| 8,313,496 B2 | * | 11/2012 | Sauer et al. ................... 606/139 |
| 2005/0154402 A1 | | 7/2005 | Sauer et al. |

FOREIGN PATENT DOCUMENTS

| | | |
|---|---|---|
| EP | 1354558 | 10/2003 |
| WO | WO 95/25468 A1 | 9/1995 |
| WO | WO 01/01868 A1 | 1/2001 |
| WO | WO 2008/045376 A2 | 4/2008 |
| WO | WO 2010/085793 A2 | 7/2010 |

* cited by examiner

*Primary Examiner* — Dianne Dornbusch
(74) *Attorney, Agent, or Firm* — Baker & Hostetler LLP

(57) ABSTRACT

The present invention provides instrumentation and associated methods for suture-based soft tissue repair. The disclosed instrument is configured to pass suture through tissue, relocate the instrument, and retrieve the suture, thereby creating a stitch. These steps can be repeated any number of times to create multiple stitches through the tissue.

47 Claims, 26 Drawing Sheets

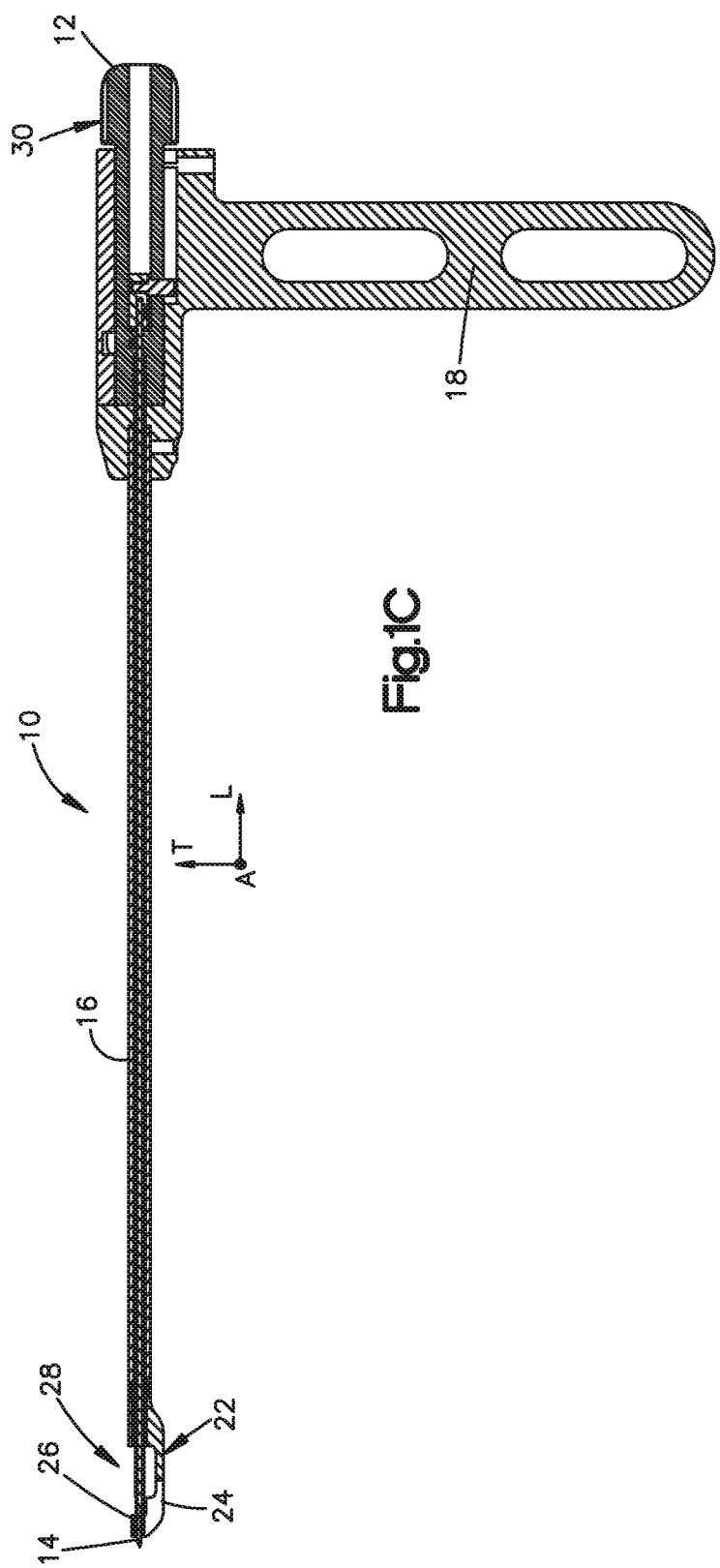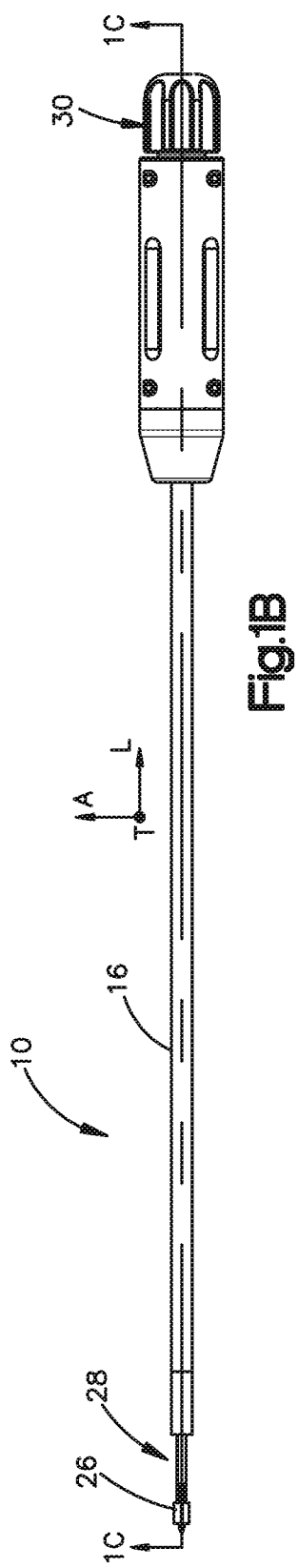

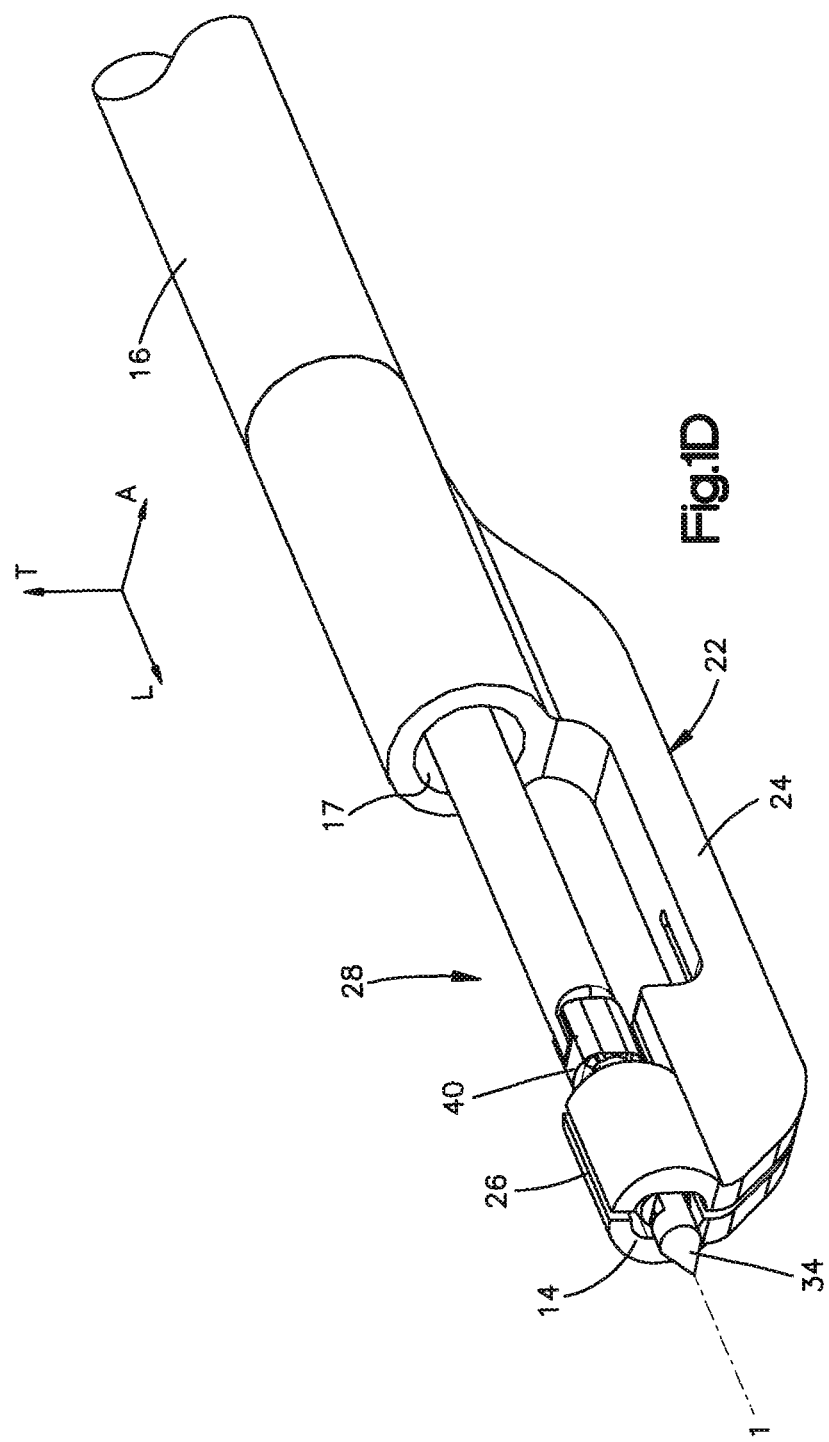

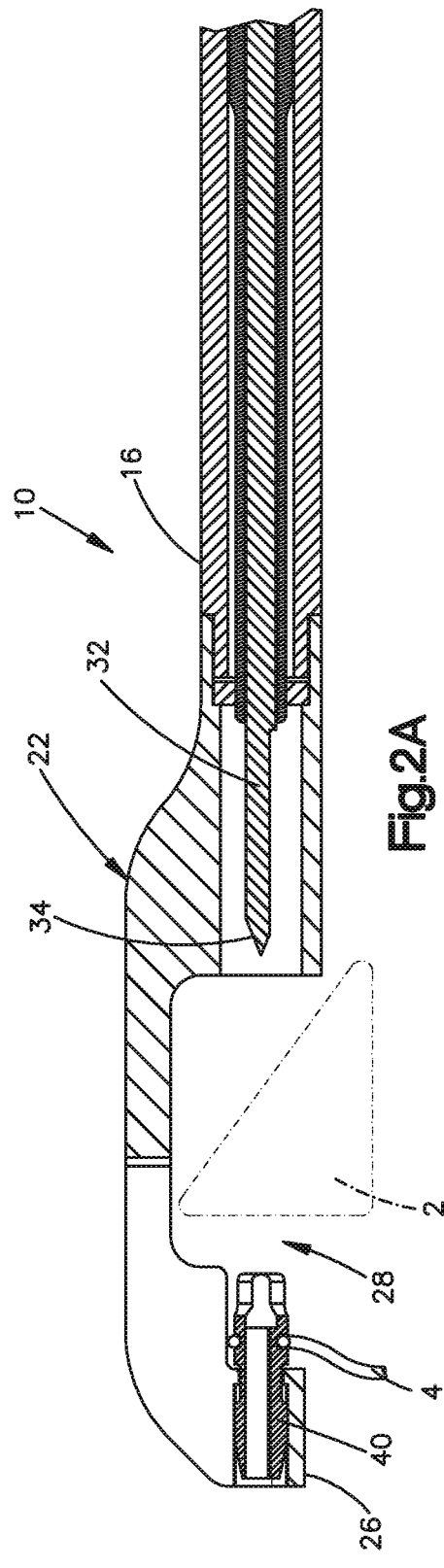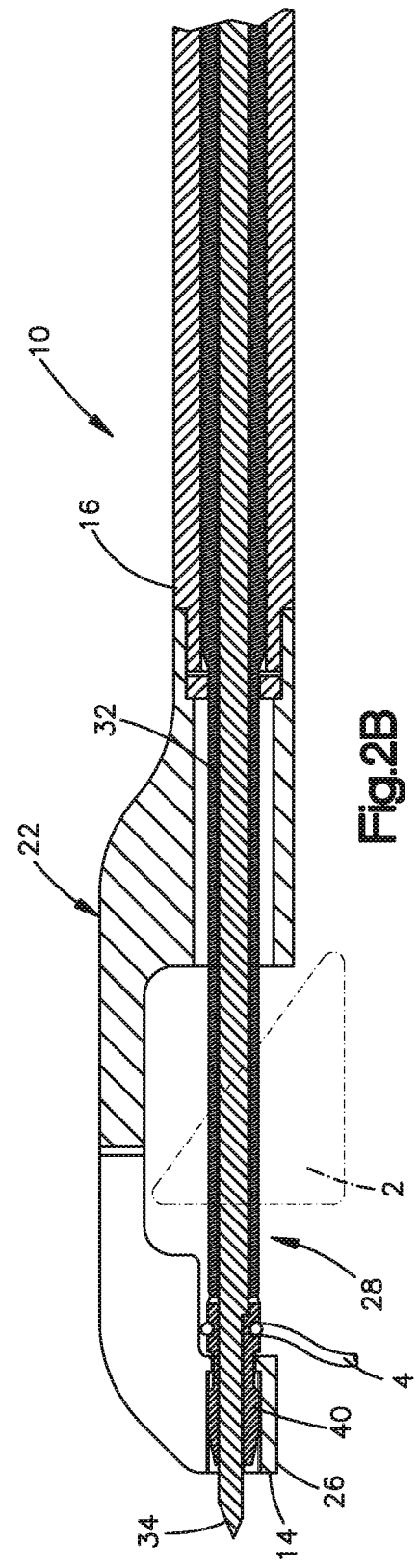

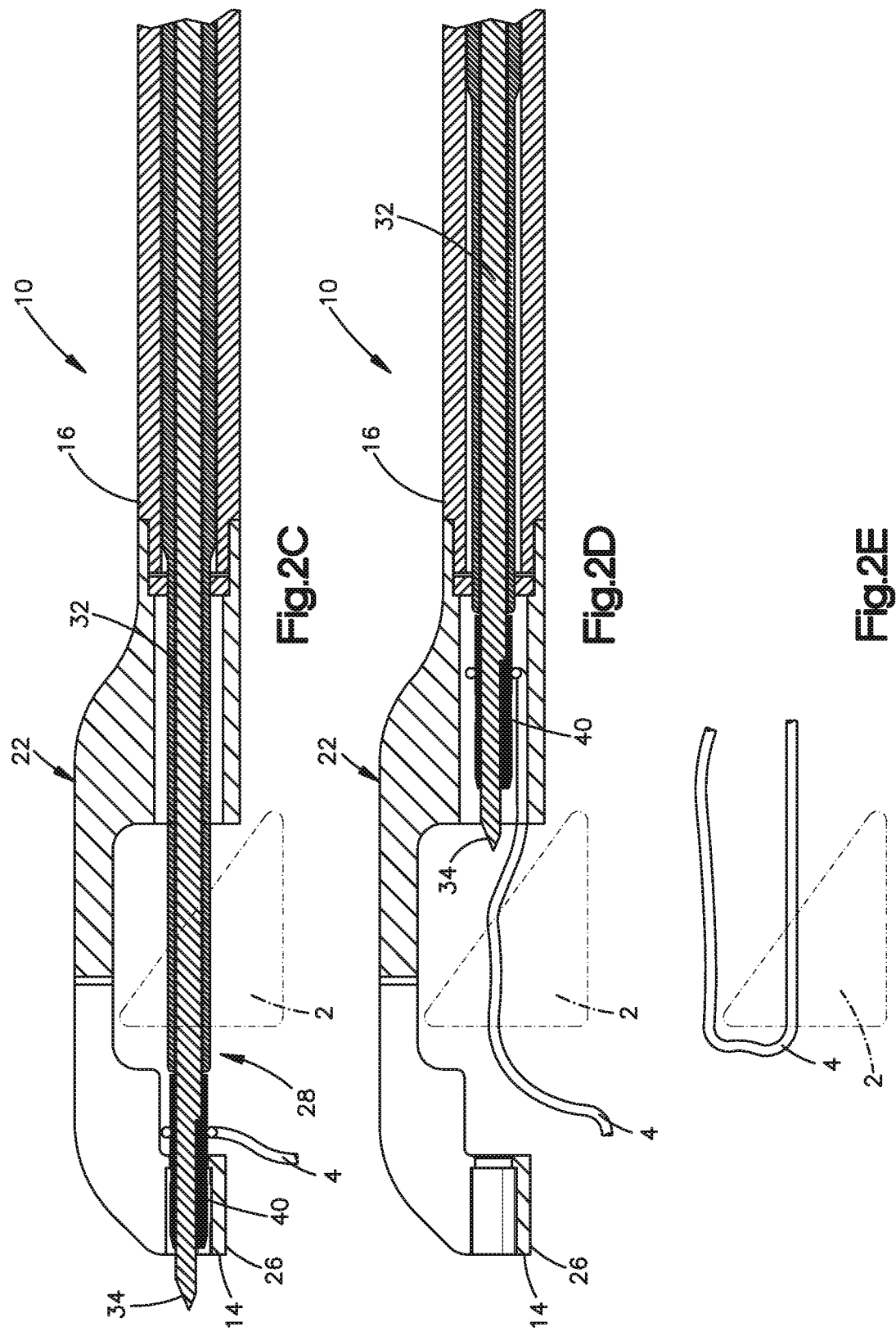

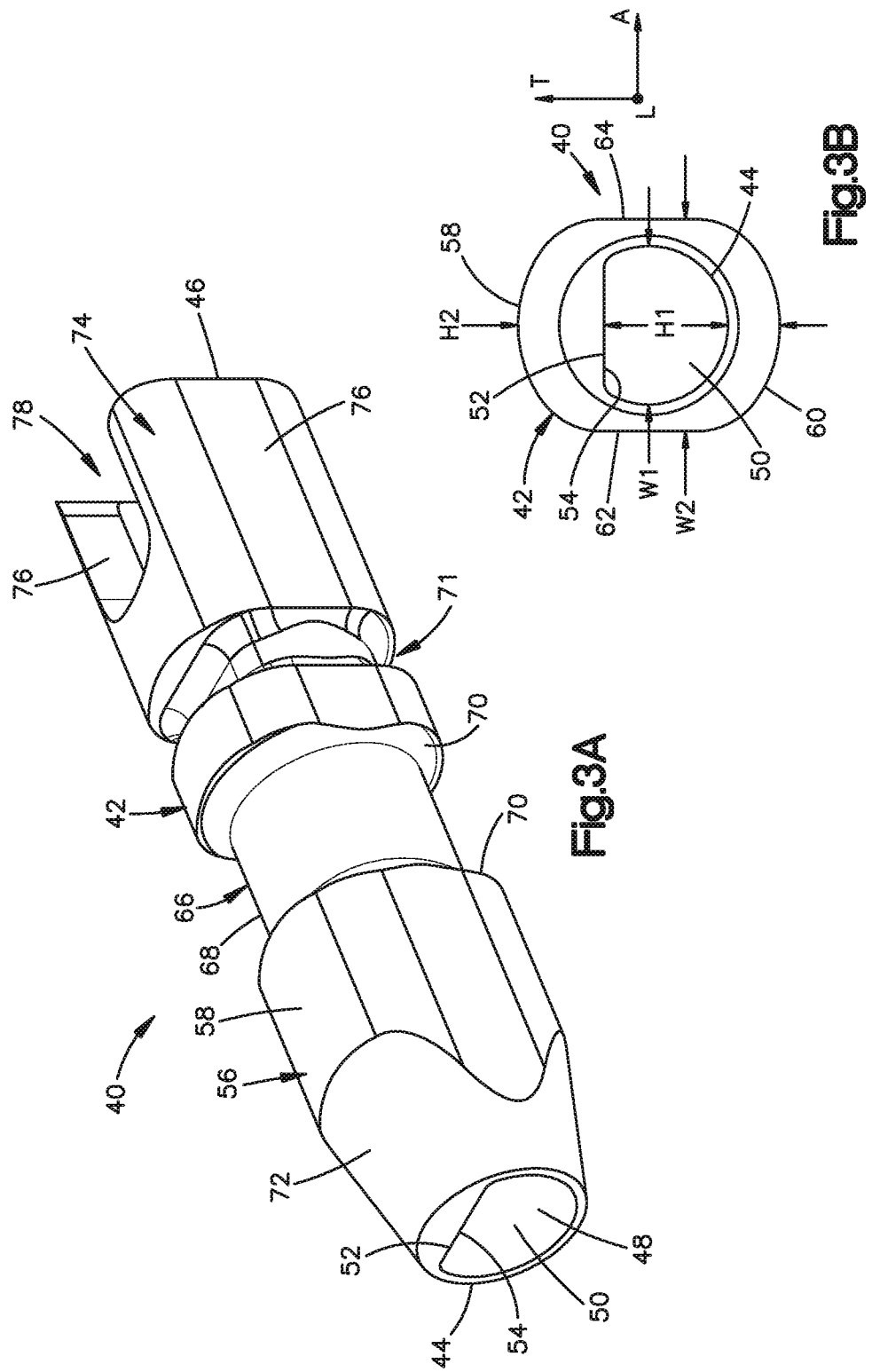

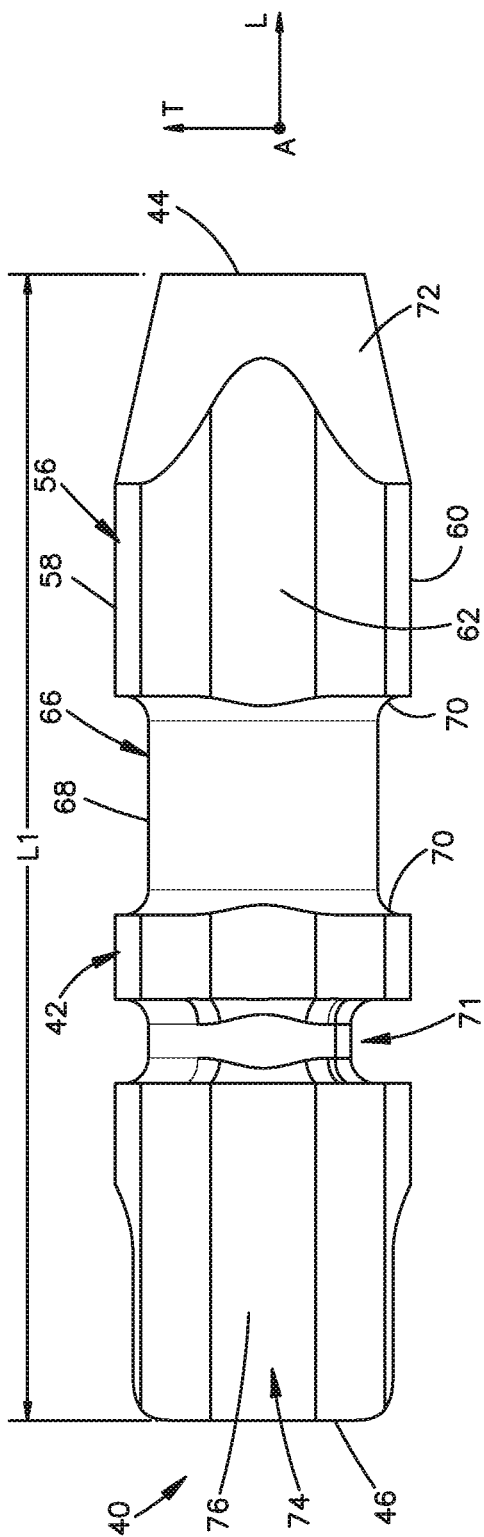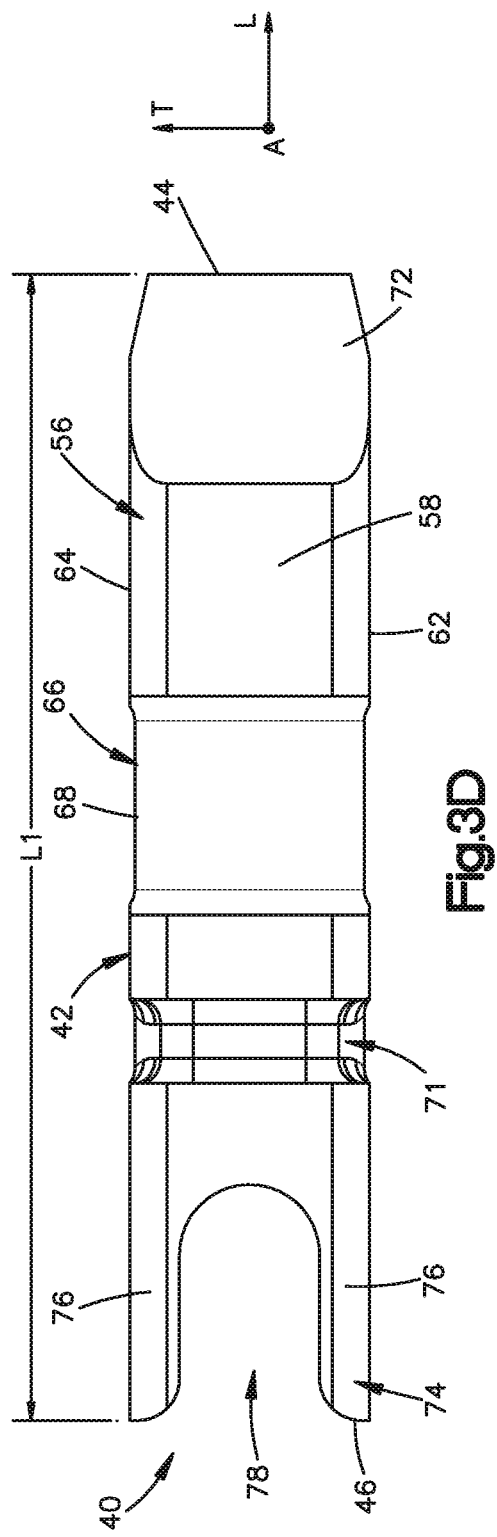

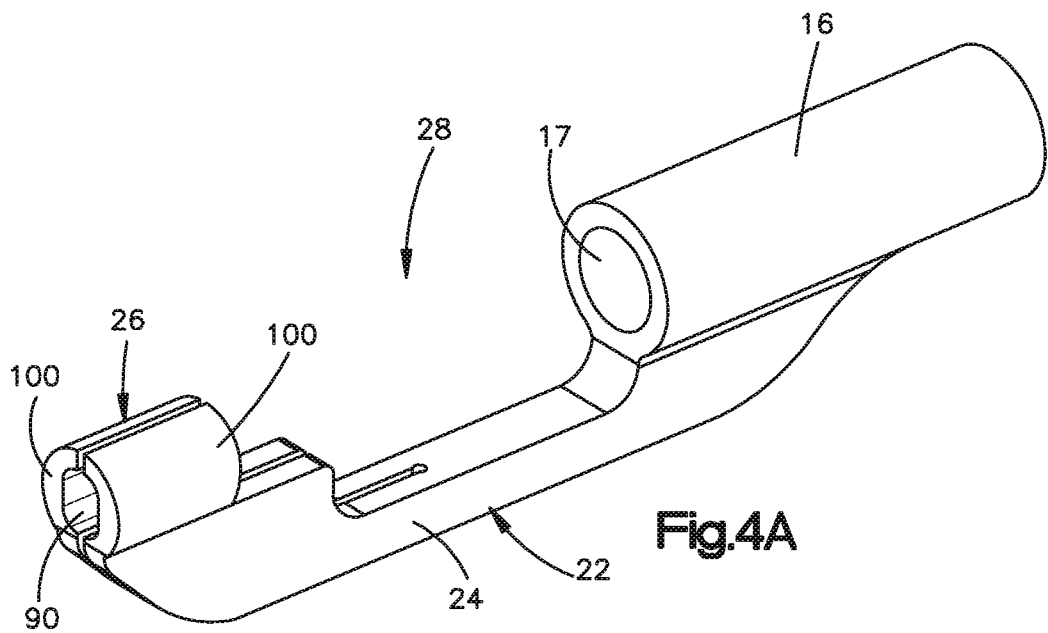
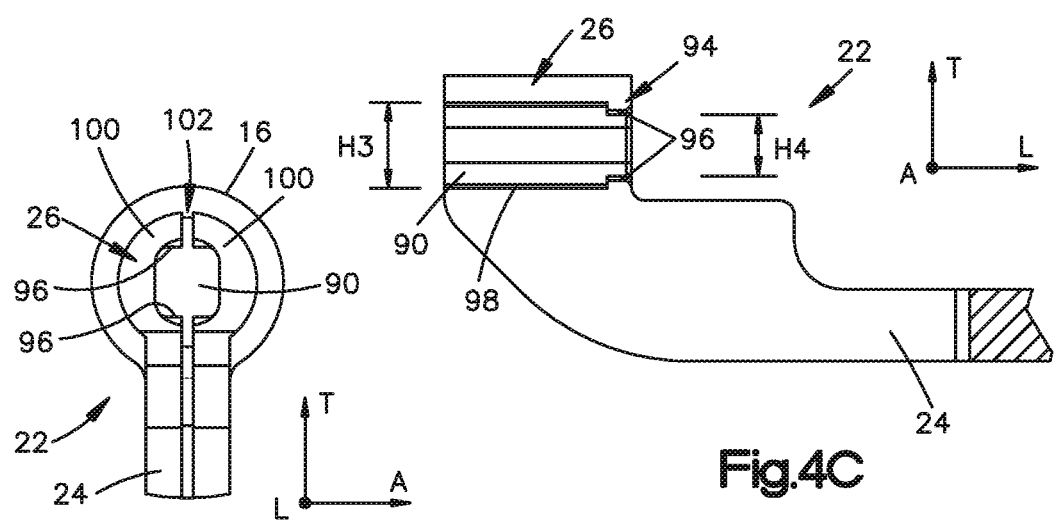
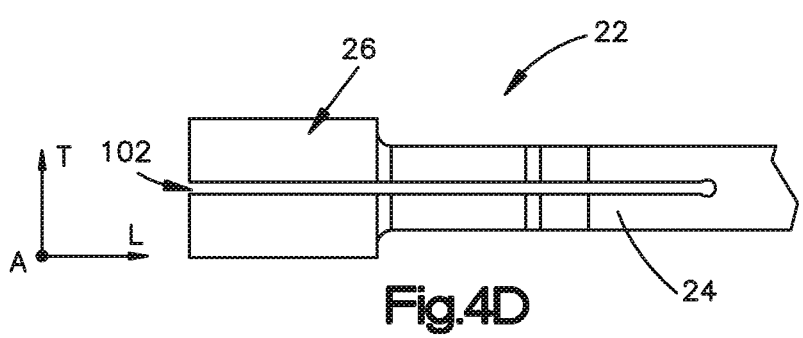
Fig.4A
Fig.4B
Fig.4C
Fig.4D

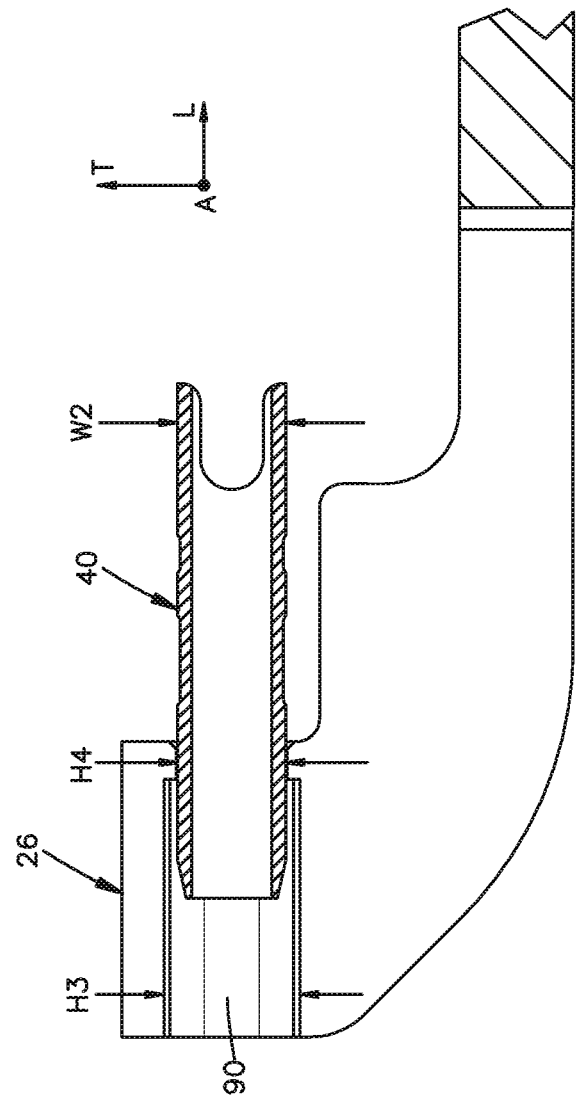
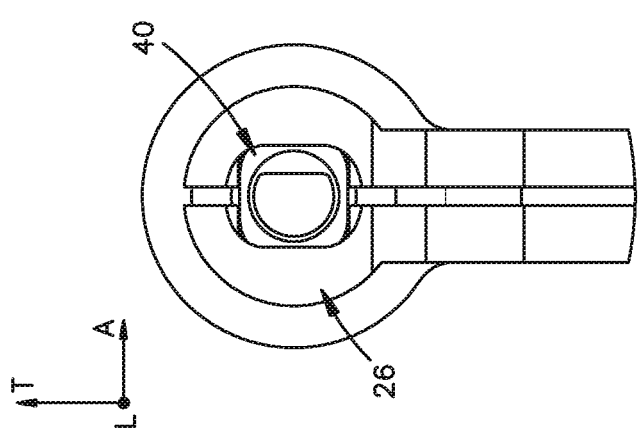
Fig.5B
Fig.5A

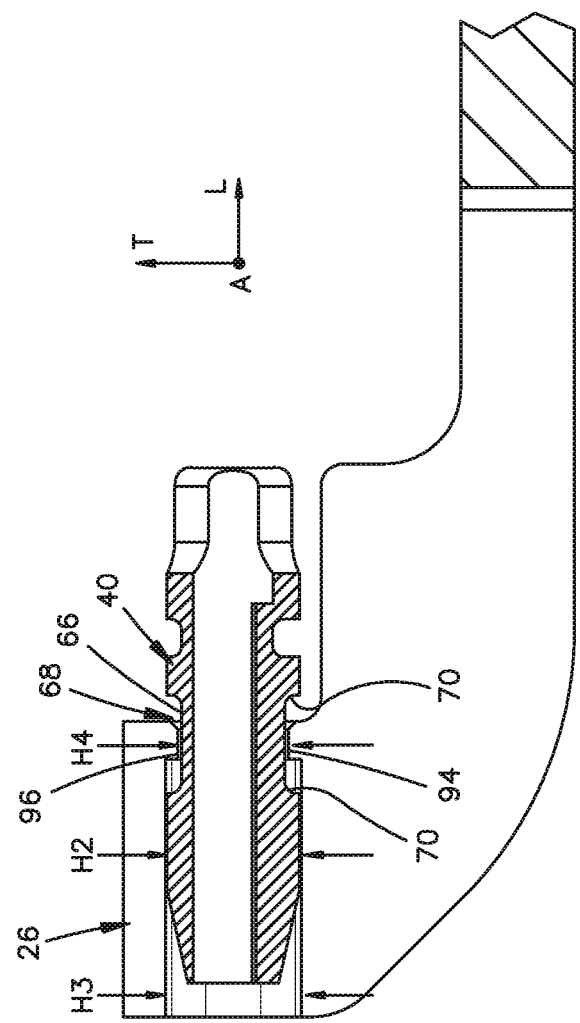
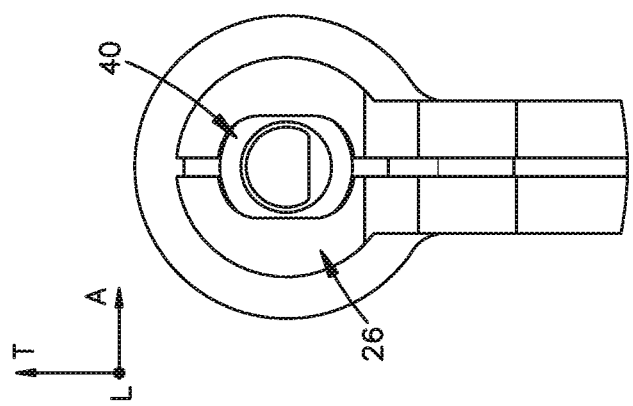
Fig.6B
Fig.6A

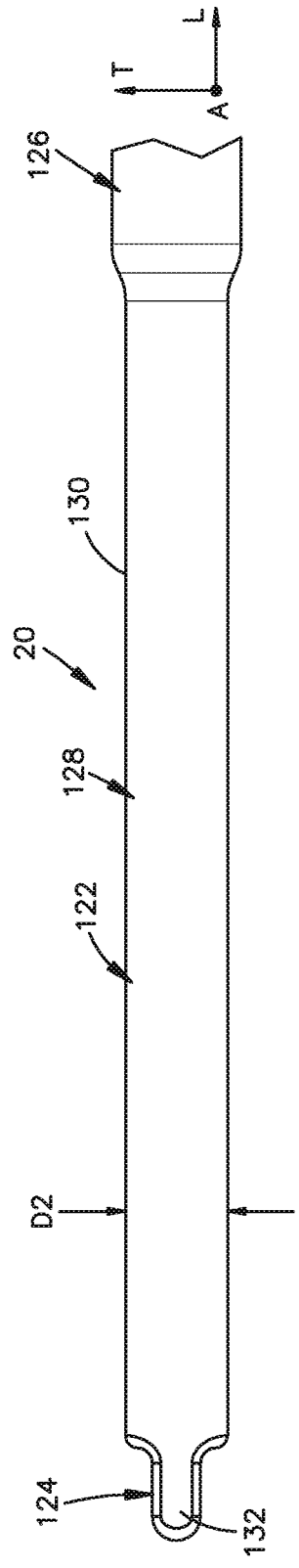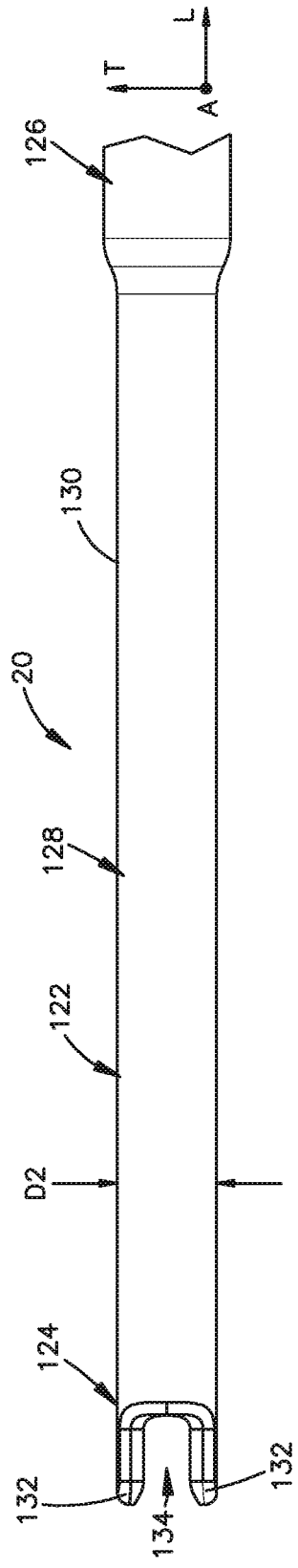

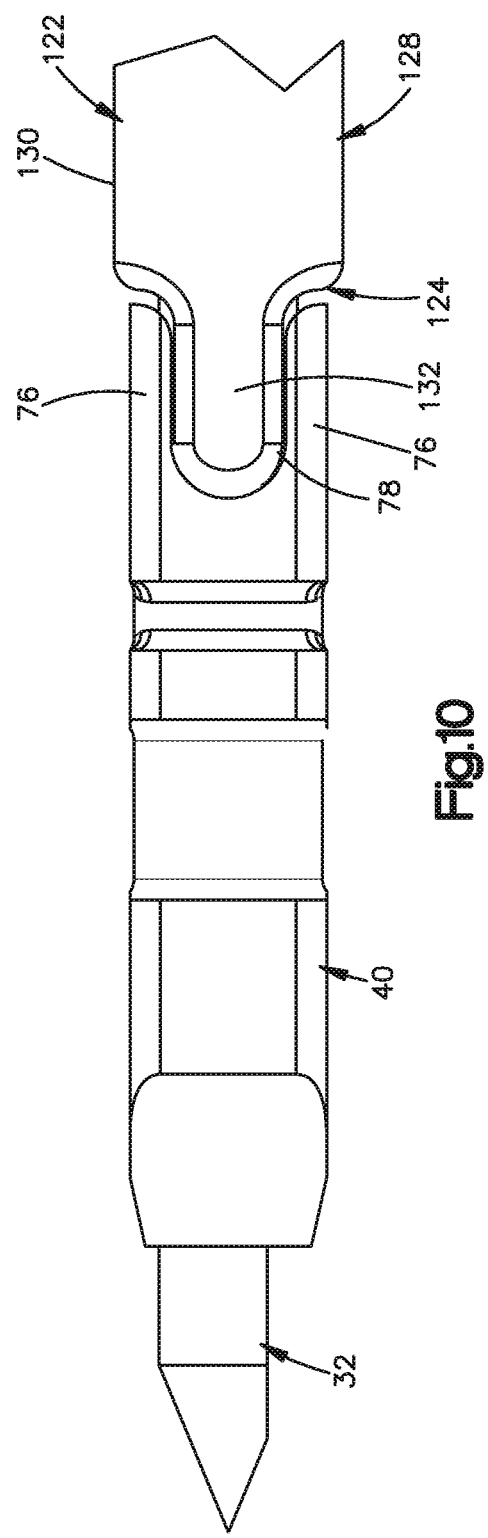

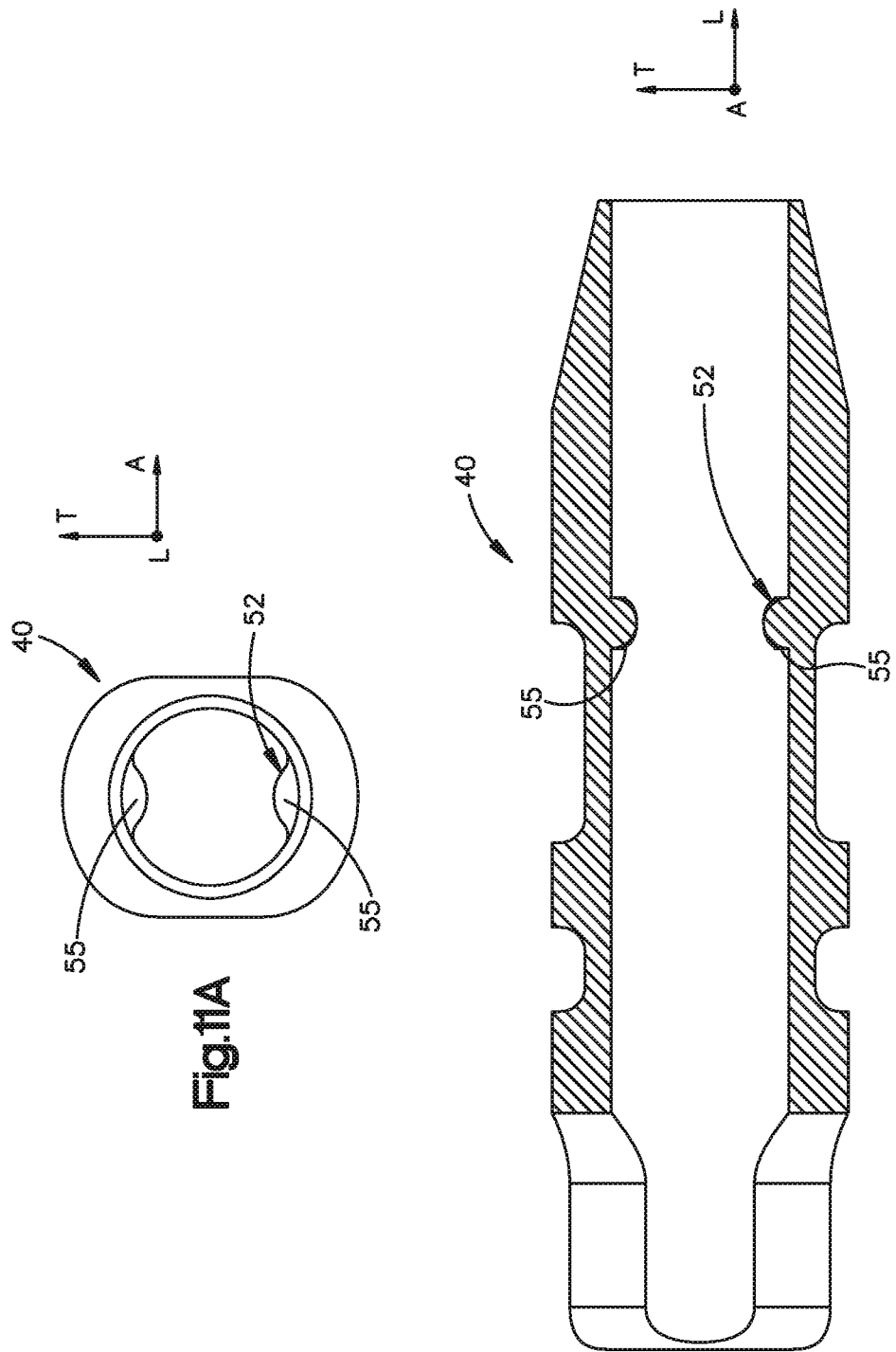

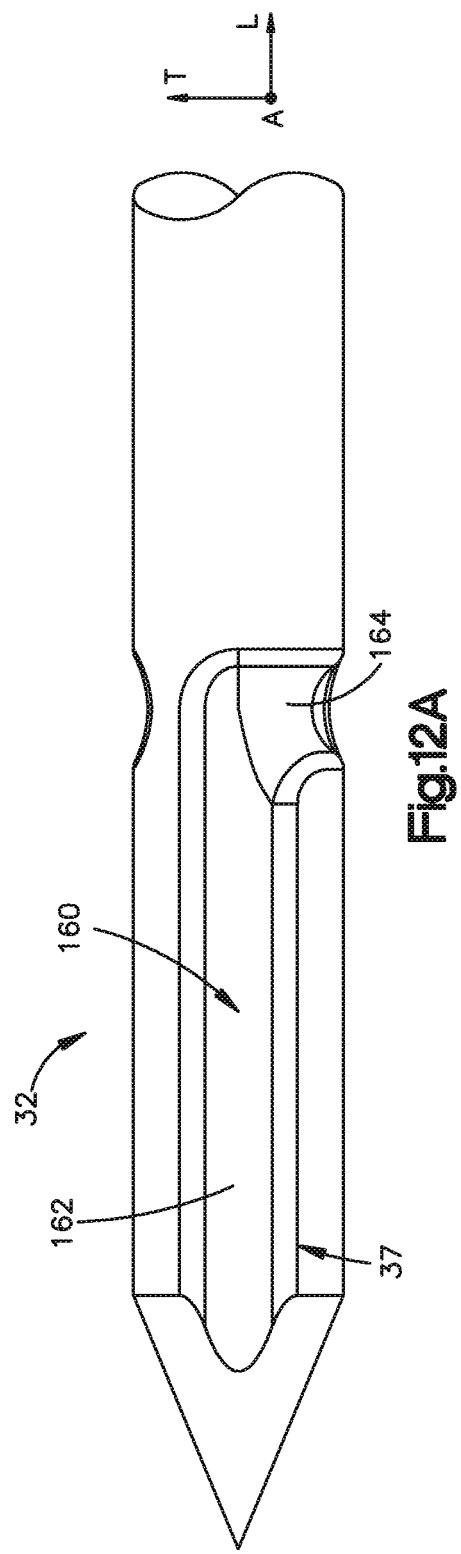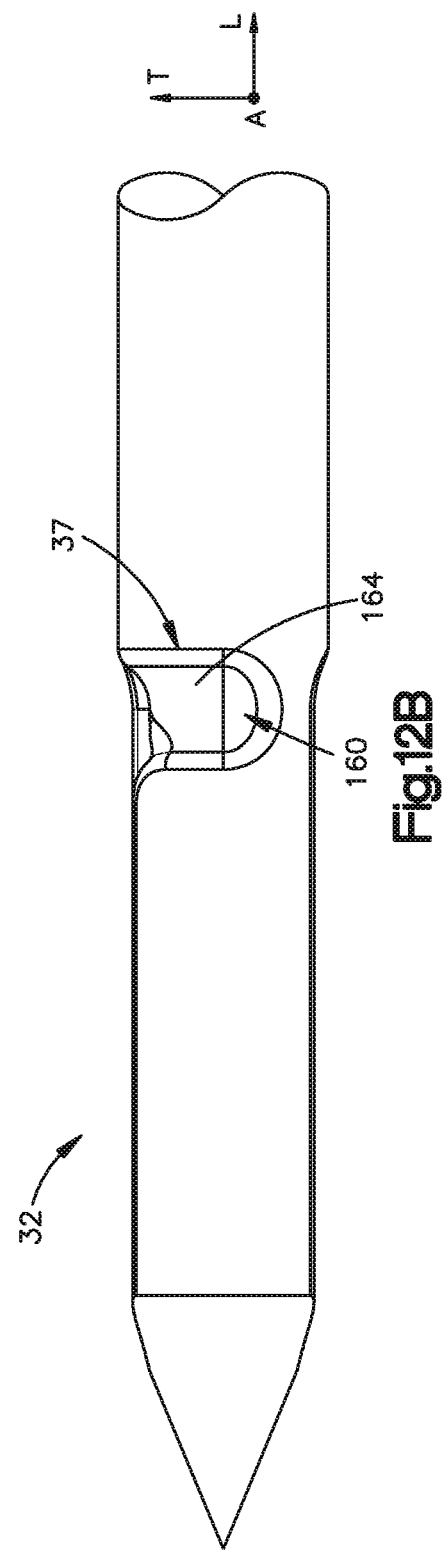

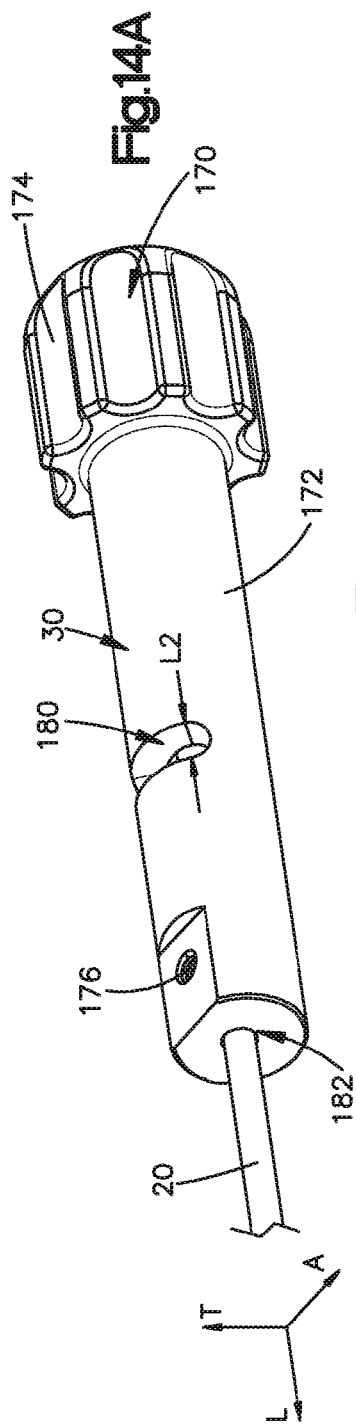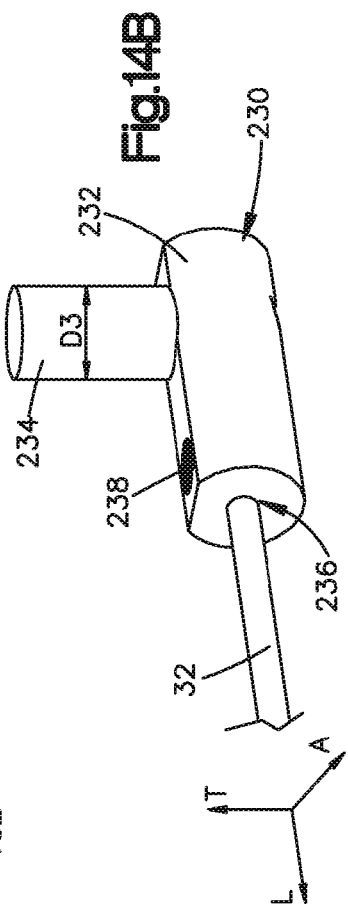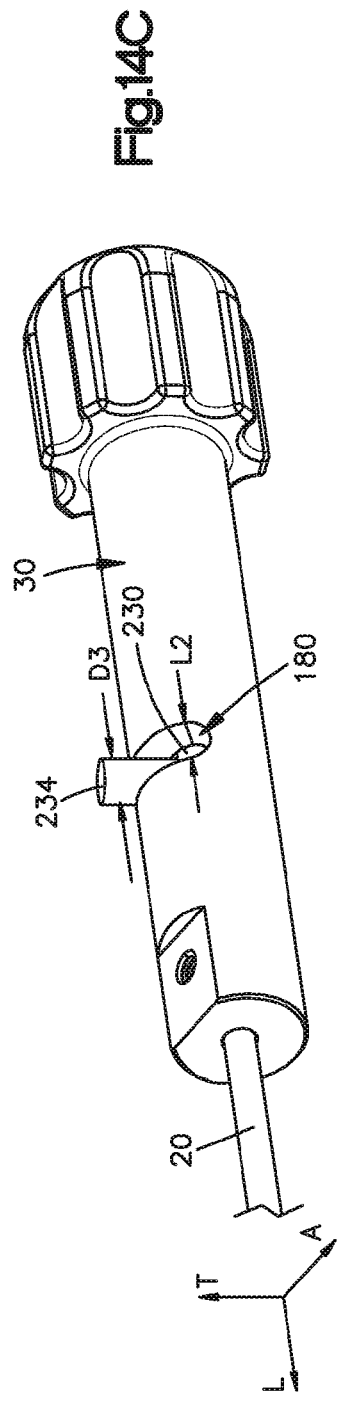

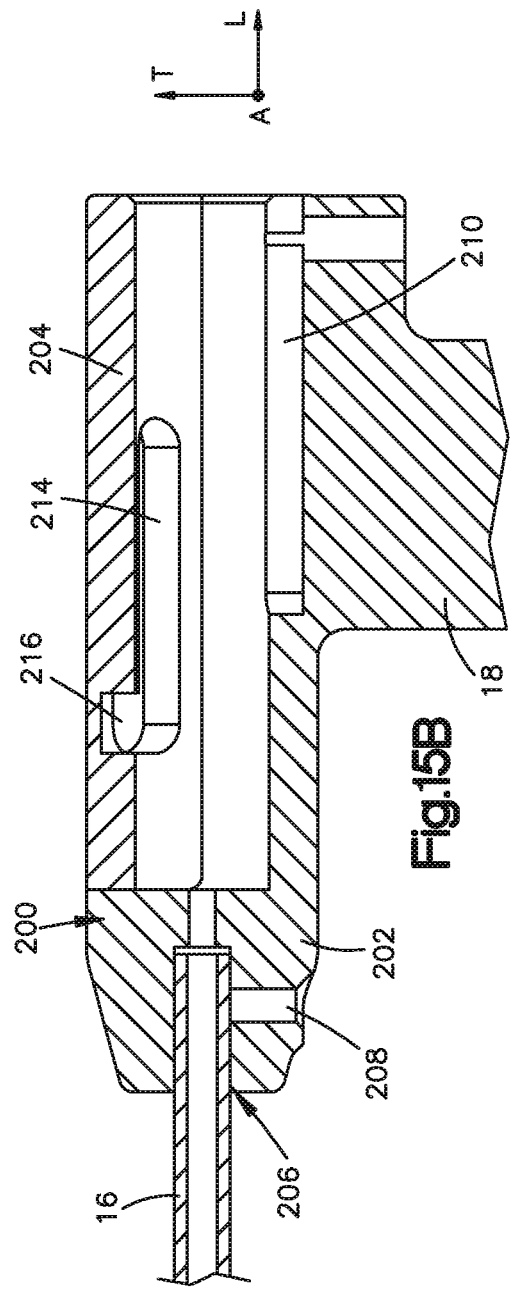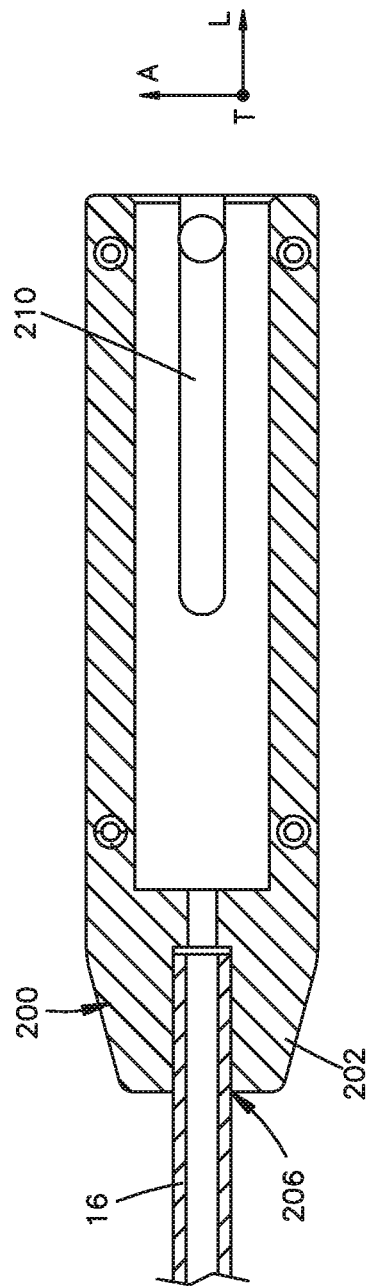
Fig.15B
Fig.15C

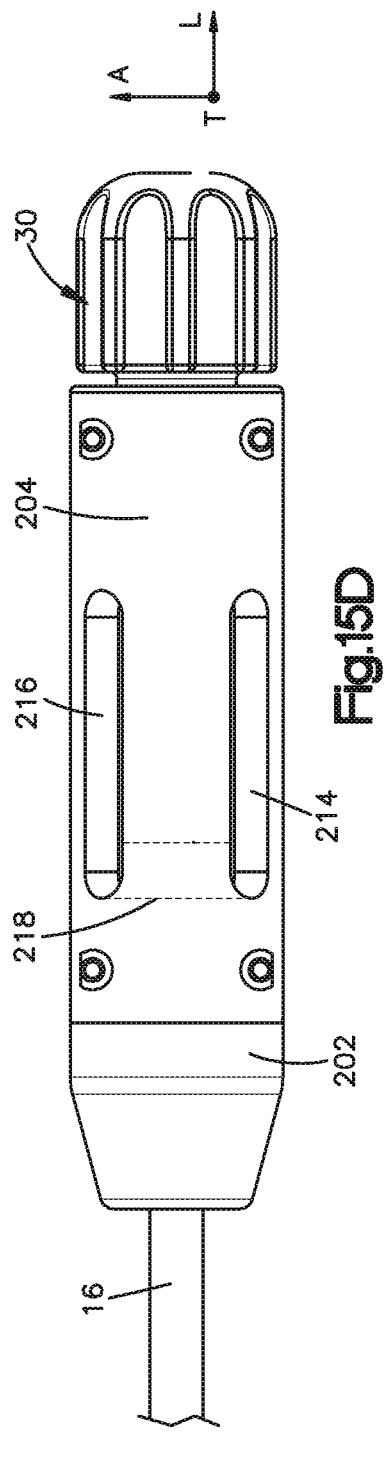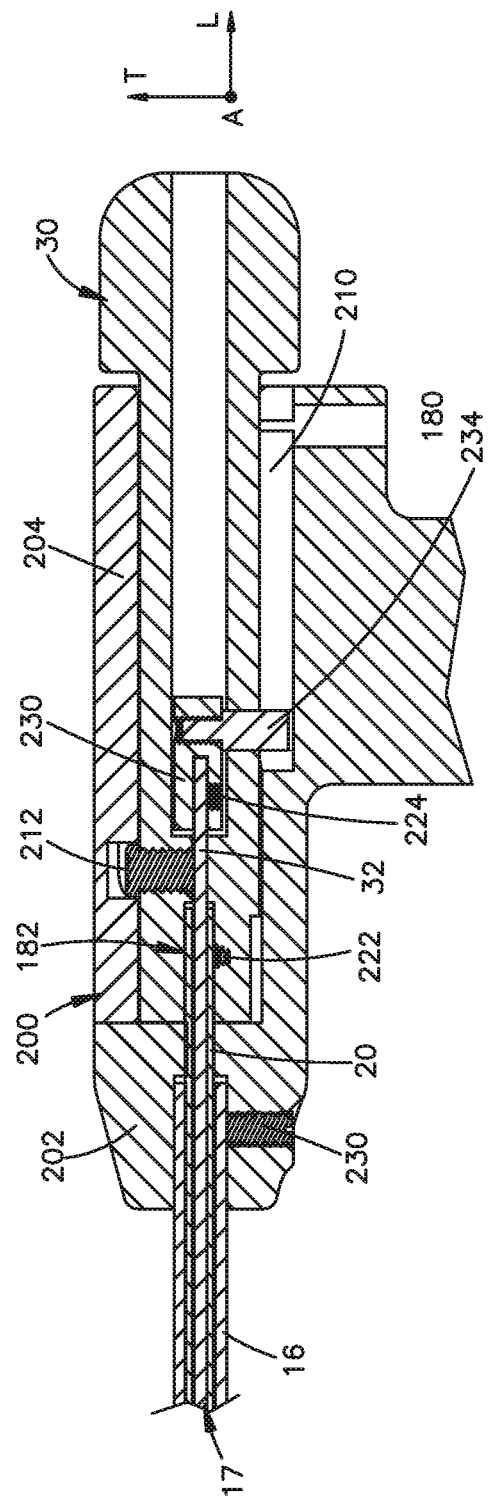

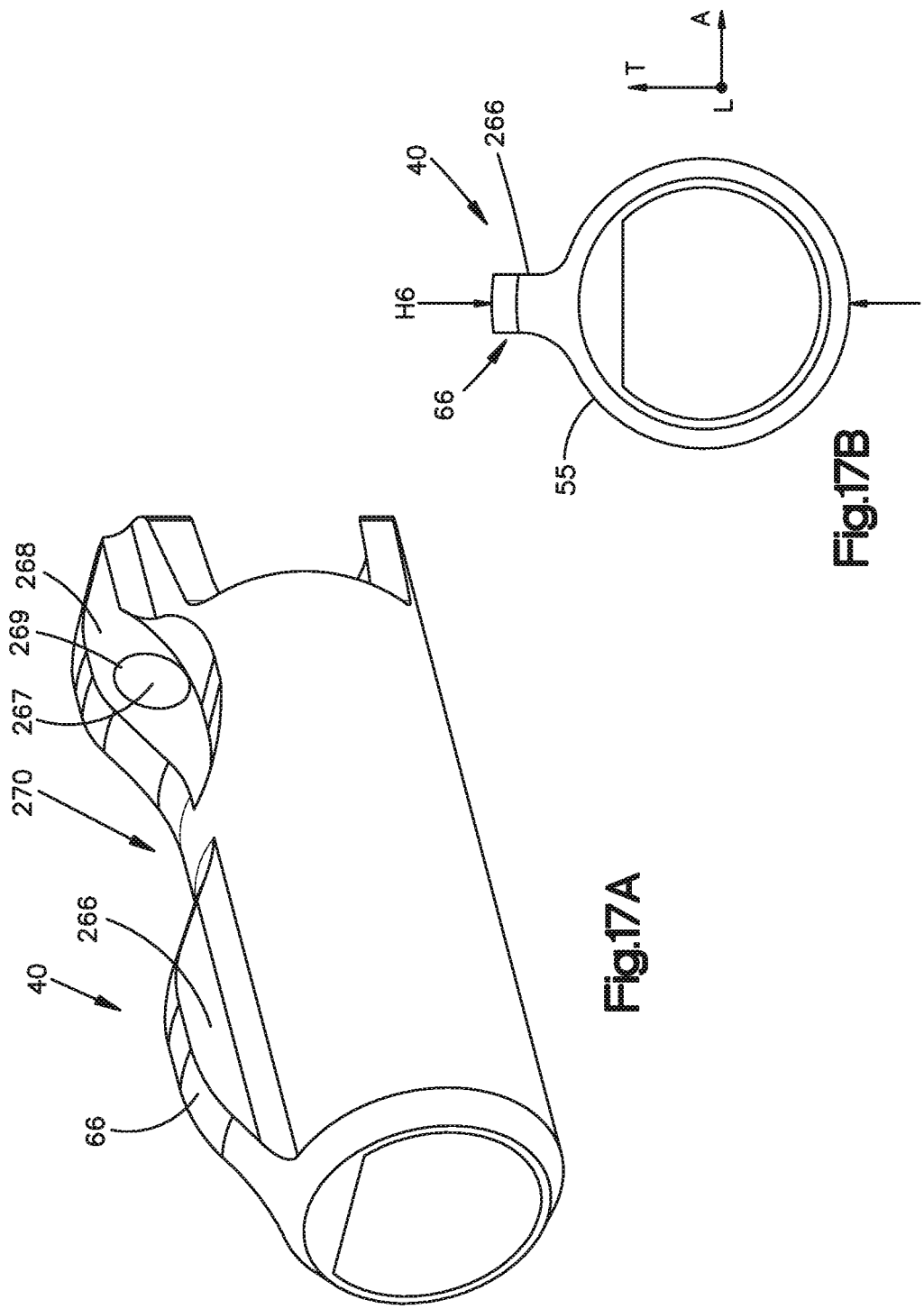

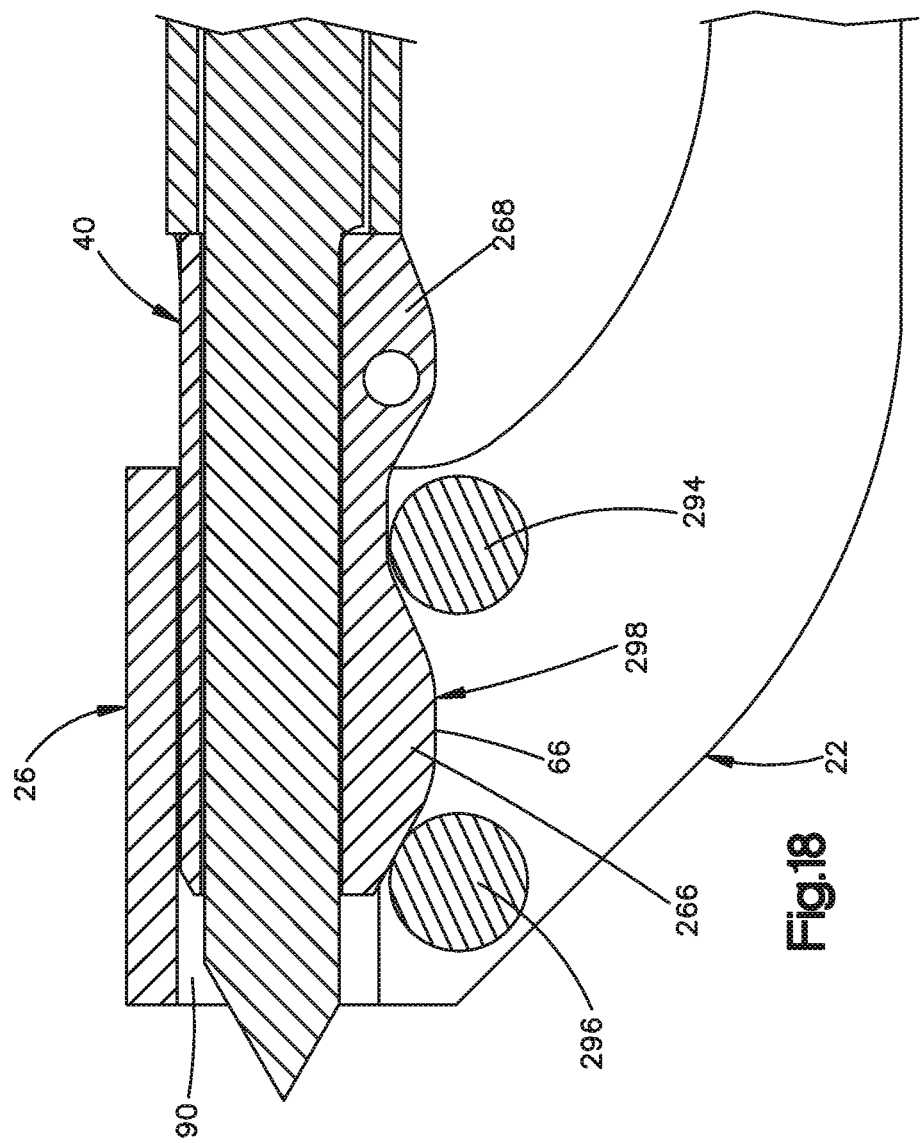

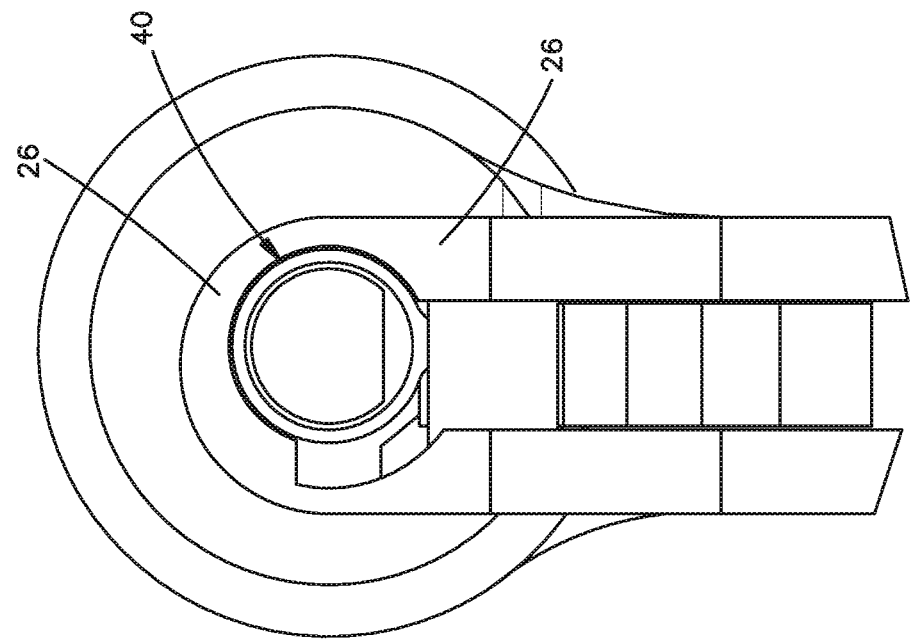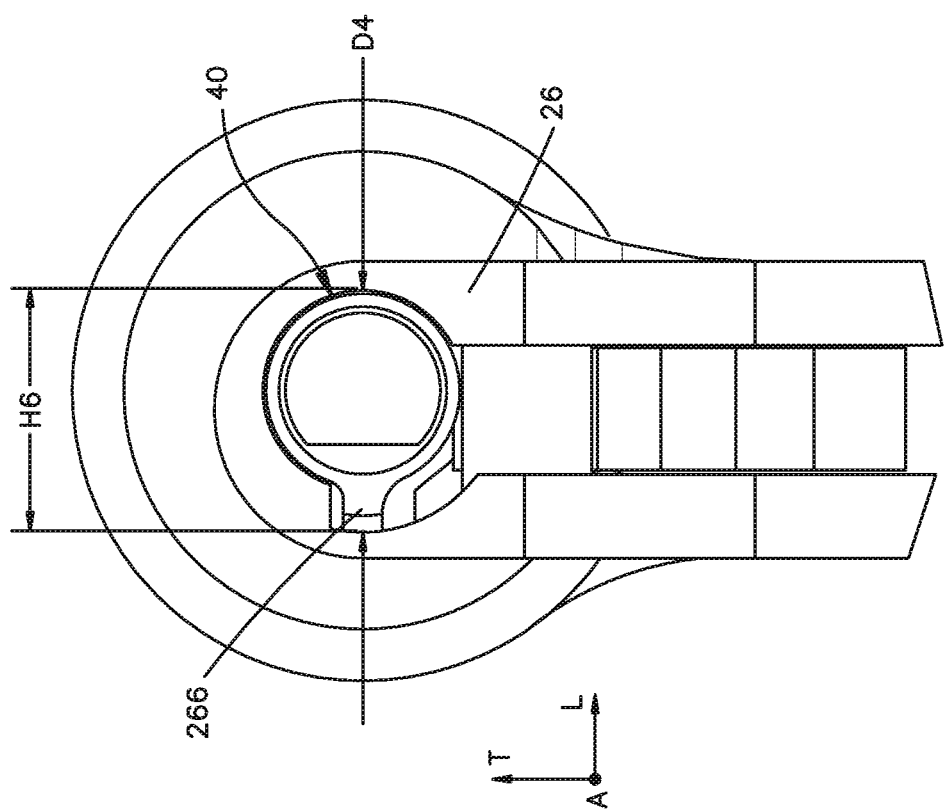

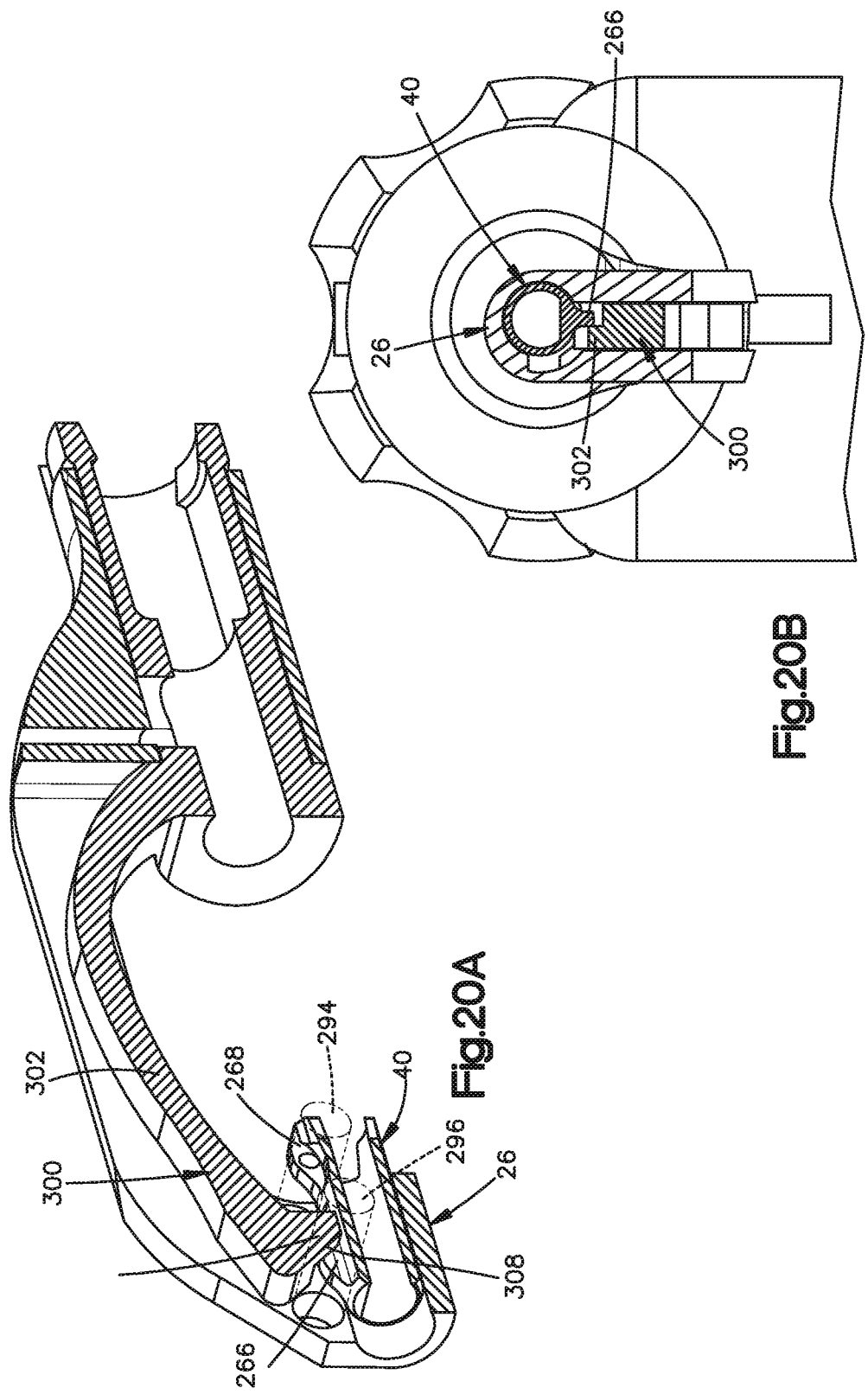

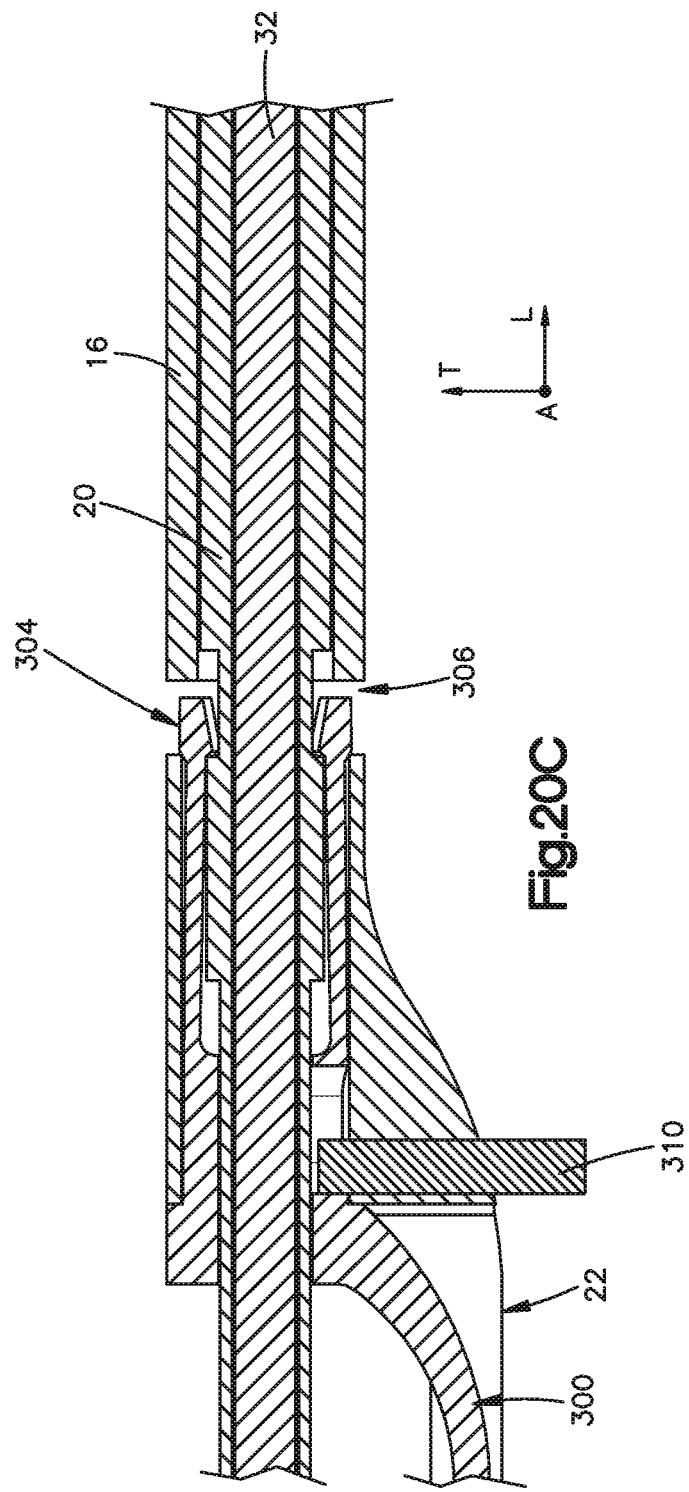

SOFT TISSUE DEFECT DEVICE AND ASSOCIATED METHOD

CROSS REFERENCE TO RELATED APPLICATIONS

This application claims benefit to U.S. Provisional Application Ser. No. 61/344,031, filed May 6, 2010, which is herein incorporated by reference in its entirety.

TECHNICAL FIELD

The present invention relates generally to orthopedics. More specifically, the present invention relates to a system and method for repair of the annulus fibrosus or the intervertebral disc and other soft tissue repair applications.

BACKGROUND

Suture passing is utilized in the repair of soft tissue defects. A suture is typically attached to either free needles or uni-directional suture passing instruments (instruments that pass suture through tissue in only one direction) for use in surgery.

A bi-directional suture passing instrument, one which can pass suture through tissue in a forward direction (away from the user), and in a rearward direction (toward the user), can have several advantages over uni-directional suture passing instruments. Many uni-directional suture passers require an additional step to manually retrieve and pass the suture in a reverse direction, thus increasing the complexity of the surgical technique and procedural time. Some uni-directional suture passer designs allow for instrumented retrieval and reloading of the suture; however these designs require that the tissue be flexible enough that it can be lifted to expose both a first and second side of the tissue to the distal end of the instrument in order to pass the suture in a reverse direction and also require an additional step to reload the suture. A bi-directional suture passing instrument eliminates the manual retrieval step, decreases the complexity of the surgical technique and the procedural time, enhances the variety of stitch configurations that can be utilized, and increases the number of bodily tissues that can be surgically repaired.

Some bi-directional suture passer designs known in the art require that a tissue defect is approached generally parallel to the tissue, which is difficult for many surgical procedures such as disc annulus repair, due to the surgical approach to the disc space. Thus, a bi-directional suture passing instrument that approaches the tissue defect generally perpendicularly could be used in additional procedural situations in which a parallel approach bi-directional suture passing instrument is inappropriate.

Yet other bi-directional suture passer designs require that a sharp needle tip be passed through tissue in both directions. This needle passing is visible in one direction and blind in the other direction, which may result in surgical complications when working in areas adjacent to nerve roots, blood vessels, bowel, or other sensitive anatomy. A bi-directional suture passing instrument that enables a sharp needle to be visible every time it is passed through tissue, thereby increasing surgical safety when operating in the areas of sensitive anatomy would be advantageous.

Furthermore, current bi-directional suture passer designs do not effectively detachably couple the suture to the needle. Thus, features for detachably coupling the suture to the needle to improve the efficiency of the instrument are also desirable.

SUMMARY

Various embodiments of a bi-directional suture passing instrument configured to approximate soft tissue defects are disclosed. In one embodiment the bi-directional suture passing instrument includes a body that defines a channel, and a boom arm that extends from the body. The boom arm has a boom arm housing that is spaced from the body and the boom arm also has an offset arm portion that extends between the body and the boom arm housing, such that a tissue-receiving gap extends between the boom arm housing and the body. A needle can be reciprocally translatable within the channel between an advanced position in which the needle extends at least into the boom arm housing, and a retracted position in which the needle is retracted from the boom arm housing. The bi-directional suture passing instrument can also include a shuttling element configured to carry a suture across the tissue-receiving gap. Movement of the shuttling element relative to both the boom arm housing and the needle can cause the shuttling element either to both lock to the boom arm housing and unlock from the needle, or both unlock from the boom arm housing and lock to the needle.

In another embodiment the bi-directional suture passing instrument can include a body that defines a channel, the channel extending along a longitudinal axis. A boom arm extends from the body, the boom arm having a boom arm housing that is spaced from the body. The boom arm also having an offset arm portion that extends between the body and the boom arm housing, such that a tissue-receiving gap extends between the boom arm housing and the body. A needle can be reciprocally translatable within the channel between an advanced position in which the needle extends at least into the boom arm housing, and a retracted position in which the needle is retracted from the boom arm housing. The bi-directional suture passing instrument can also include a shuttling element configured to carry a suture across the tissue-receiving gap. A single rotational movement of the shuttling element relative to both the boom arm housing and the needle can cause the shuttling element either to both lock to the boom arm housing and unlock from the needle, or both unlock from the boom arm housing and lock to the needle.

In another embodiment the bi-directional suture passing instrument includes a body that defines a channel, and a boom arm extending from the body. The boom arm can include a boom arm housing that is spaced from the body, the boom arm housing having an inner surface defining a bore, and the inner surface having a first engagement member. The boom arm housing can also have an offset arm portion extending between the body and the boom arm housing such that a tissue-receiving gap is disposed between the boom arm housing and the body. A needle can be reciprocally translatable within the channel between an advanced position in which the needle extends at least into the boom arm housing, and a retracted position in which the needle is retracted from the boom arm housing, the needle defining an outer surface with a second engagement member. The bi-directional suture passing instrument can also include a shuttling element configured to carry a suture across the tissue-receiving gap, the shuttling element having an outer surface including a third engagement member and an inner surface defining an inner bore and including a fourth engagement member. In a first angular orientation of the bi-directional suture passing instrument the first and third engagement members are mated such that the boom arm housing and the shuttling element can be separated only by rotation of the shuttling element relative to the boom arm housing, and in a second angular orientation of the bi-directional suture passing instrument the second and fourth engagement members are mated such that the needle and the shuttling element can be separated only by rotation of the shuttling element relative to the needle.

Methods of passing a suture through a soft tissue defect are also disclosed. For example, in one embodiment the method includes the steps of advancing a needle and a shuttling element that are detachably coupled, through the soft tissue defect and into a boom arm housing. The shuttling element is then rotated relative to both the needle and the boom arm housing such that the shuttling element both locks to the boom arm housing and unlocks from the needle. The needle is then retracted from the boom arm housing and the shuttling element back through the soft tissue defect while the shuttling element remains coupled to the boom arm housing.

In another embodiment the method of passing a suture through a soft tissue defect includes advancing a needle through the soft tissue defect and into a shuttling element and a boom arm housing that are detachably connected. The shuttling element is then rotated relative to both the needle and the boom arm housing such that the shuttling element both locks to the needle and unlocks from the boom arm housing. The needle and shuttling element is then retracted from the boom arm housing back through the soft tissue defect.

BRIEF DESCRIPTION OF THE DRAWINGS

The foregoing summary, as well as the following detailed description of illustrative embodiments of the bi-directional suture passing instrument of the present application, will be better understood when read in conjunction with the appended drawings. For the purposes of illustrating the bi-directional suture passing instrument of the present application, there is shown in the drawings illustrative embodiments. It should be understood, however, that the application is not limited to the precise arrangements and instrumentalities shown. In the drawings:

FIG. 1B is a top plan view of the bi-directional suture passing instrument illustrated in FIG. 1A.

FIG. 1C is a side cross-sectional view along line 1C-1C of the bi-directional suture passing instrument illustrated in FIG. 1B;

FIG. 1D is an enlarged perspective view of the body, the boom arm, the needle, the sheath, and the shuttling element illustrated in FIG. 1A;

FIG. 2A is a cross-sectional view of a soft tissue defect positioned adjacent the bi-directional suture passing instrument illustrated in FIG. 1A, with the needle in a retracted position within the body and the shuttling element positioned within and locked to the boom arm housing;

FIG. 2B is a cross-sectional view of the bi-directional suture passing instrument illustrated in FIG. 1A with the needle in an advanced position within the shuttling element and the boom arm housing and the shuttling element locked to the boom arm housing;

FIG. 2C is a cross-sectional view of the bi-directional suture passing instrument illustrated in FIG. 1A with the needle in an advanced position within the shuttling element and the boom arm housing and the shuttling element locked to the needle;

FIG. 2D is a cross-sectional view of the bi-directional suture passing instrument illustrated in FIG. 1A with the needle in a retracted position within the shuttling element and the body and the shuttling element locked to the needle;

FIG. 2E is a cross-sectional view of the soft tissue defect illustrated in FIG. 2A with a suture extending through the soft tissue defect;

FIG. 3A is a perspective view of the shuttling element illustrated in FIG. 1D, according to one embodiment;

FIG. 3B is a front view of the shuttling element illustrated in FIG. 3A;

FIG. 3C is a side view of the shuttling element illustrated in FIG. 3A;

FIG. 3D is a top view of the shuttling element illustrated in FIG. 3A;

FIG. 4A is a side perspective view of the boom arm illustrated in FIG. 1A;

FIG. 4B is a front view of the boom arm illustrated in FIG. 4A;

FIG. 4C is a cross-sectional view of the boom arm illustrated in FIG. 4A;

FIG. 4D is a top view of the boom arm illustrated in FIG. 4A;

FIG. 5A is a front view of the shuttling element and the boom arm illustrated in FIG. 1D, in an unlocked configuration;

FIG. 5B is a cross-sectional view of the shuttling element and the boom arm illustrated in FIG. 5A, in an unlocked configuration;

FIG. 6A is a front view of the shuttling element and the boom arm illustrated in FIG. 1D, in a locked configuration;

FIG. 6B is a cross-sectional view of the shuttling element and the boom arm illustrated in FIG. 6A, in a locked configuration;

FIG. 9A is a top view of a sheath of the bi-directional suture passing instrument;

FIG. 9B is a side view of the sheath illustrated in FIG. 9A;

FIG. 10 is a side elevation view of the sheath, the shuttling element, and the needle illustrated in FIG. 1D;

FIG. 11A is a front view of the shuttling element illustrated in FIG. 1D, according to another embodiment;

FIG. 11B is a cross-sectional view of the shuttling element illustrated in FIG. 11A;

FIG. 12A is a top plan view of the needle illustrated in FIG. 1D, according to another embodiment;

FIG. 12B is a side elevation view of the needle illustrated in FIG. 12A;

FIG. 14A is a perspective view of the actuator illustrated in FIG. 1A;

FIG. 14B is a perspective view of a connector;

FIG. 14C is a perspective view of the actuator illustrated in FIG. 14A and the connector illustrated in FIG. 14B in an assembled configuration;

FIG. 15B is a side cross-sectional view of the handle, the body, and the housing illustrated in FIG. 15A;

FIG. 15C is a top cross-sectional view of the handle, the body, and the housing illustrated in FIG. 15A;

FIG. 15D is a top view of the handle, the body, and the housing illustrated in FIG. 15A and the actuator illustrated in FIG. 14;

FIG. 16 is a side cross-sectional view of a proximal portion of the bi-directional suture passing instrument illustrated in FIG. 1A;

FIG. 17A is a perspective view of the shuttling element illustrated in FIG. 1D in accordance with another embodiment;

FIG. 17B is a front view of the shuttling element illustrated in FIG. 17A;

FIG. 18 is a cross-sectional view of the shuttling element illustrated in FIG. 17A and the boom arm housing illustrated in FIG. 1D according to another embodiment;

FIG. 19A is a front view of the shuttling element and boom arm housing illustrated in FIG. 18 in an unlocked configuration;

FIG. 19B is a front view of the shuttling element and boom arm housing illustrated in FIG. 19A in a locked configuration;

FIG. 20A is a side cross-sectional view of the shuttling element and the boom arm housing illustrated in FIG. 18 and a secondary locking mechanism;

FIG. 20B is a front cross-sectional view of the shuttling element, the boom arm housing and the secondary locking mechanism illustrated in FIG. 20A;

FIG. 20C is a side cross-sectional view of the secondary locking mechanism illustrated in FIG. 20A and the sheath 20 illustrated in FIG. 1A.

DETAILED DESCRIPTION OF ILLUSTRATIVE EMBODIMENTS

Figure 1A:
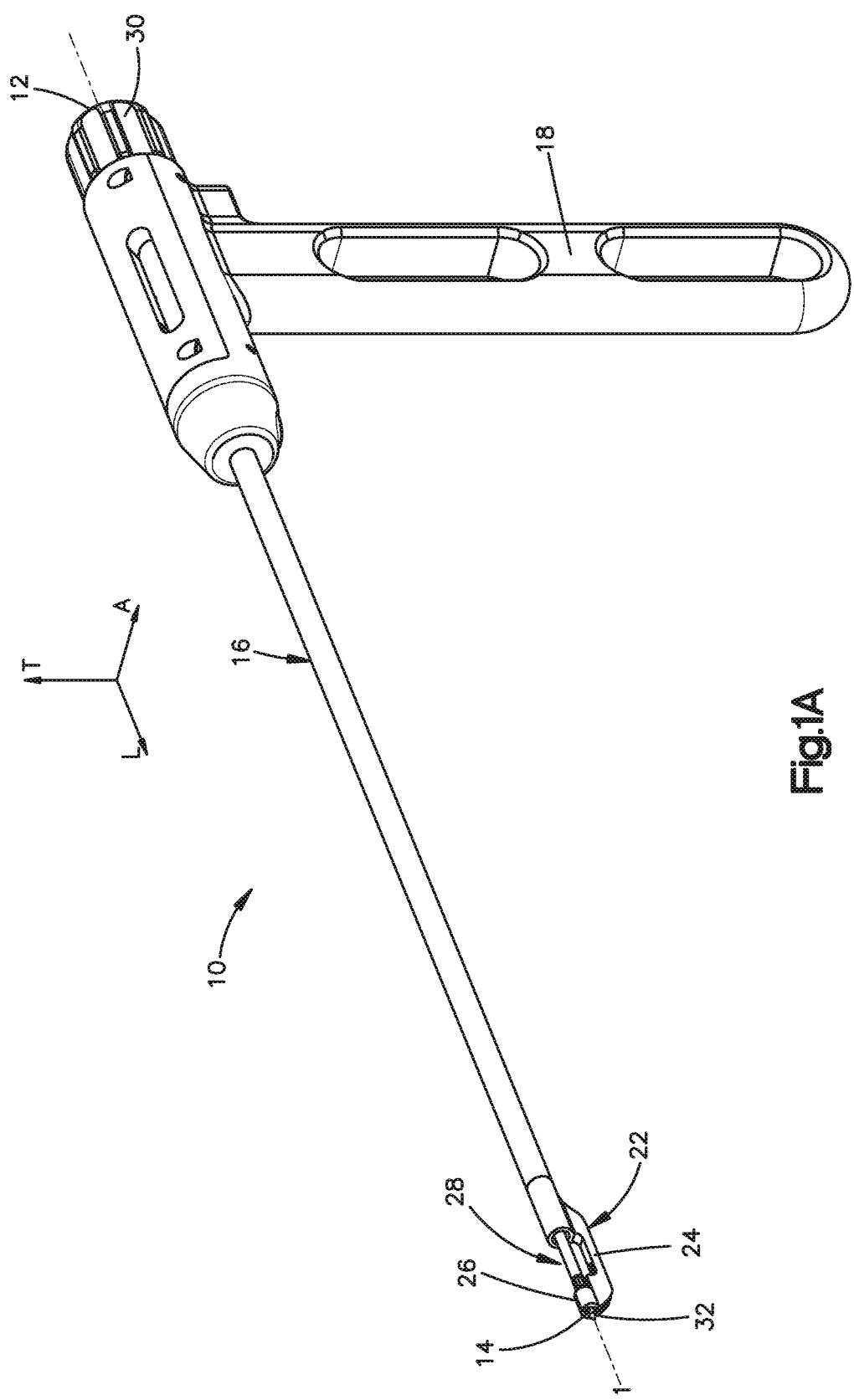
FIG. 1A is a side perspective view of a bi-directional suture passing instrument in accordance with one embodiment, including a body, a handle, a boom arm, a needle, a shuttling element, a sheath, and an actuator.

Certain terminology is used in the following description for convenience only and is not limiting. The words "right", "left", "lower" and "upper" designate directions in the drawings to which reference is made. The words "inwardly" or "distally" and "outwardly" or "proximally" refer to directions toward and away from, respectively, the patient's body, or the geometric center of the bi-directional suture passing instrument and related parts thereof. The words, "anterior", "posterior", "superior", "inferior" and related words and/or phrases designate illustrative positions and orientations in the human body to which reference is made and are not meant to be limiting. The terminology includes the above-listed words, derivatives thereof and words of similar import. Additionally, a three dimensional coordinate system is used to describe the positions and orientations of the parts of the bi-directional suture passing instrument. The coordinate system includes a longitudinal direction L, a lateral direction A, and a transverse direction T, wherein each of the directions is perpendicular to both of the other two directions.

Referring to FIGS. 1A-1D, a bi-directional suture passing instrument 10 extends in a longitudinal direction L, and includes a proximal end 12 and a distal end 14. As shown, the instrument 10 includes a body 16 with a channel 17, the body 16 and channel 17 can be elongate in the longitudinal direction L along a longitudinal axis 1, a handle 18 can be coupled to the body 16, and a boom arm 22 can be coupled to the body 16, spaced apart from the handle 18. The boom arm 22 includes an arm 24 that is coupled to the body 16 and carries a boom arm housing 26, so as to define a tissue-receiving gap 28 between the body 16 and the boom arm housing 26. The instrument 10 can further include an actuator 30 and a needle 32 coupled to the actuator 30 by a sheath 20. The actuator 30 and the needle 32 are reciprocally translatable between a retracted (rearward) position and an extended or advanced (forward) position, within the channel 17 of the body 16. The instrument 10 further includes a shuttling element 40 that is configured to carry a strand of suture to be inserted through a tissue defect. As will be described in more detail below, when the shuttling element 40 is coupled to the needle 32, the shuttling element 40 may pass through a tissue defect. Once the shuttling element 40 has passed through the tissue defect, the shuttling element 40 may be detachably coupled to the boom arm housing 26.

Referring to FIGS. 2A-2E, the bi-directional suture passing instrument 10 can be used as shown to pass a suture 4 through a soft tissue defect 2. In FIG. 2A the bi-directional suture passing instrument 10 has been positioned adjacent a soft tissue defect 2 such that the soft tissue defect 2 is disposed within the tissue-receiving gap 28 of the boom arm 22. As shown, the needle 32 is in a retracted position such that a tip 34 of the needle 32 is housed within the body 16 and does not protrude into the tissue-receiving gap 28. This arrangement of the needle 32 within the body 16 prevents any undesired damage to the soft tissue defect 2 while the bi-directional suture passing instrument 10 is being positioned. Alternatively, the retracted position of the needle 32 can include the needle being disposed at least partially within the tissue-receiving gap 28 but still spaced from the boom arm housing 26. Also as shown, the shuttling element 40 is positioned within and locked to the boom arm housing 26.

Referring to FIG. 2B, the needle 32 is in an advanced position. From the retracted position, the needle translates from the body 16, through the tissue-receiving gap 28 and the soft tissue defect 2, and the needle 32 is then received within the shuttling element 40 and the boom arm housing 26. The advanced position of the needle 32 can include the tip 34 of the needle 32 extending all the way through the boom arm housing 26 such that the tip 34 protrudes from the distal end 14 of the instrument 10 as shown. Alternatively, in the advanced position the tip 34 of the needle 32 may be housed within the boom arm housing 26 such that the tip 34 does not protrude from the distal end 14, thereby preventing any undesired damage to tissue that is adjacent the soft tissue defect 2. As shown, the needle 32 is free to translate through the shuttling element 40 and the boom arm housing 26 while the shuttling element 40 and the boom arm housing 26 remain locked together.

Referring to FIG. 2C, the shuttling element 40 can be moved with respect to both the needle 32 and the boom arm housing 26 to both unlock the shuttling element 40 from the boom arm housing 26 and lock the shuttling element 40 to the needle 32. As shown, the shuttling element 40 has been rotated with respect to the needle 32 and the boom arm housing 26 such that translation of the needle 32 back through the tissue-receiving gap 28 and the soft tissue defect 2 will cause the shuttling element 40 to also translate through the tissue-receiving gap 28 and the soft tissue defect 2. The needle 32 and shuttling element 40 are free to translate through the boom arm housing 26.

Referring to FIG. 2D, the needle 32 has translated back through the tissue-receiving gap 28 and the soft tissue defect 2, with the shuttling element 40 locked to the needle. As the shuttling element passes through the soft tissue defect 2 the suture 4 which is secured to the shuttling element 40 also passes through the soft tissue defect 2. As shown the needle 32 is once again in the retracted position along with the shuttling element 40.

Referring to FIG. 2E, the suture 4 has passed through the soft tissue defect 2. The suture 4 can be secured to the soft tissue defect 2 to hold the suture 4 in place. The suture 4 can be secured by knotting the suture 4. For example the suture may contain a pre-knotted sliding knot (not shown) on one end of the suture. Alternately opposing ends of the suture 4 can be tied together into a knot.

Thus referring again to FIGS. 2A-2E, a method of passing a suture 4 through a soft tissue defect 2 includes: advancing a needle 32 through the soft tissue defect 2 and into a shuttling element 40 and a boom arm housing 26, the shuttling element 40 and the boom arm housing 26 being detachably connected, and the suture 4 being secured to the shuttling element 40; rotating the shuttling element 40 relative to both the needle 32 and the boom arm housing 26 such that the shuttling element 40 both locks to the needle 32 and unlocks from the boom arm housing 26; and retracting the needle 32 and the shuttling element 40 from the boom arm housing 26 back through the soft tissue defect 2. Further steps of the method can include advancing the needle 32 and the shuttling element 40 across the soft tissue defect 2 and into the boom arm housing 26; rotating the shuttling element 40 relative to both the needle 32 and the boom arm housing 26 such that the shuttling element 40 both unlocks from the needle 32 and locks to the boom arm housing 26; and retracting the needle 32 from the boom arm housing 26 and the shuttling element 40 through the soft tissue defect 2.

Alternatively, a method of passing a suture 4 through a soft tissue defect 2 can include the steps: advancing a needle 32 and a shuttling element 40 through the soft tissue defect 2 and into a boom arm housing 26, the shuttling element 40 and the needle 32 being detachably coupled, and the suture 4 being secured to the shuttling element 40; rotating the shuttling element 40 relative to both the needle 32 and the boom arm housing 26 such that the shuttling element 40 both locks to the boom arm housing 26 and unlocks from the needle 32; and retracting the needle 32 from the boom arm housing 26 back through the soft tissue defect 2 while the shuttling element 40 remains coupled to the boom arm housing 26. Further steps of the method can include advancing the needle 32 across the soft tissue defect 2 and into the boom arm housing 26; rotating the shuttling element 40 relative to both the needle 32 and the boom arm housing 26 such that the shuttling element 40 both unlocks from the boom arm housing 26 and locks to the needle 32; and retracting the needle 32 and the shuttling element 40 from the boom arm housing 26 and through the soft tissue defect 2.

Referring to FIGS. 3A-3D, a shuttling element 40 can include a body 42 that extends from a distal tip 44 to a proximal end 46. The body 42 can have an inner surface 48 that defines a bore 50 that extends through a length L1 of the body 42, the length L1 being measured from the distal tip 44 to the proximal end 46. The bore 50 is sized and configured to slidably receive a wire (such as the needle 32 which is described in detail below). As shown the bore 50 is D-shaped such that a height H1 of the bore 50 is less than a width W1 of the bore 50, wherein the height H1 and the width W1 are measured at an angular offset to each other. As shown that height H1 and the width W1 are measured perpendicular to each other, with the height H1 being measured in the transverse direction T and the width W1 being measured in the lateral direction A. Alternatively, the bore 50 can be any shape such that the bore 50 has a different height H1 and width W1. The inner surface 48 of the body 42 can include an engagement member 52 (also referred to as the fourth engagement member 52). The fourth engagement member 52 as shown is a raised flat 54. Alternatively, the fourth engagement member 52 could be a recess, a groove, a protrusion, a notch, a recessed flat, or any other structure that is matable with a corresponding engagement member 37 of the needle 32 (explained in greater detail below and also referred to as the second engagement member 37).

The body 42 of the shuttling element 40 also has an outer surface 56. The outer surface 56 can include a top surface 58 and a bottom surface 60. A height H2 of the shuttling element 40 is measured from the top surface 58 to the bottom surface 60 along the transverse direction T. The outer surface 56 can further include a first side surface 62 and a second side surface 64. A width W2 of the shuttling element is measured from the first side surface 62 to the second side surface 64 along the lateral direction A. As shown the top surface 58 and the bottom surface 60 are curved while the first side surface 62 and the second side surface 64 are flat. Alternatively, the top surface 58, bottom surface 60, first side surface 62 and second side surface 64 can be either all curved, partially curved, all flat, or any combination of curved, partially curved and flat. The outer surface 56 can also include an engagement member 66 (also referred to as the third engagement member 66). The third engagement member 66 as shown is a recessed radial groove 68. The recessed radial groove 68 extends between opposing retention walls 70. Alternatively, the third engagement member 66 could be a linear recess, a groove, a protrusion, a notch, a recessed flat, or any other structure that is matable with a corresponding engagement member 94 of the boom arm housing 26 (explained in greater detail below and also referred to as the first engagement member 94).

The shuttling element 40 can also include a securing member 71 that enables the suture 4 to be secured to the shuttling element 40 during operation of the bi-directional suture passing instrument 10 and passage of the shuttling element 40 through the soft tissue defect 2. As shown the securing member 71 can be a recess in the outer surface 56. Alternatively, the securing member can be a groove, a protrusion, a notch, a hook, or any other structure that would allow the suture 4 to be secured to the shuttling element 40. In use the suture 4 can be placed in the securing member 71 and then a knot is tied in the suture 4 such that the suture cannot come loose from the shutting element without untying the knot or cutting the suture 4. The bi-directional suture passing instrument 10 can come preassembled with the suture 4 secured to the shuttling element 40 or with the shuttling element 40 being provided separately or without a suture 4. Alternatively, the instrument 10 may be provided with a plurality of shuttling elements 40, each with a strand of suture 4 secured thereto.

The body 42 of the shuttling element 40 can also include a distal portion 72 adjacent the distal tip 44 and a proximal portion 74 adjacent the proximal end 46. The distal portion 72 can be tapered such that the shuttling element 40 is narrower at the distal tip 44 and gradually gets wider. This tapering of the shuttling element 40 can result in passage of the shuttling element 40 through a soft tissue defect 2 to take less force and causes less damage to the soft tissue defect 2. The proximal portion 74 can include flanges 76 that define an actuation slot 78. The actuation slot 78 is configured to receive an actuation member (such as sheath 20 which is described in greater detail below) that can be used to translate the shuttling element 40 in the longitudinal direction L or rotate the shuttling element 40 about the longitudinal direction L.

Referring to FIGS. 4A-4D, the boom arm 22 extends from the body 16. The boom arm 22 can include an arm 24 that is coupled to the body 16 and extends distally along the longitudinal direction L to a boom arm housing 26. The boom arm housing 26 is configured to receive the shuttling element 40. The arm 24 is offset from the body 16 in the transverse direction T such that a tissue-receiving gap 28 is disposed between the boom arm housing 26 and the body 16. The tissue-receiving gap 28 is configured to receive a soft tissue defect 2, such as a laceration in the skin or meniscus, that is to be repaired by the suturing instrument 10. Additionally, the bi-directional suture passing instrument 10 can be used to repair other tears, fissures, defects, lacerations, or incisions in or through a variety of soft tissues, such as but not limited to, annulus fibrosus, meniscus, rotator cuff, fascia, skin, vessels, cartilage, ligaments, tendons, and joint capsules.

The boom arm housing 26 defines a cylindrical or alternatively shaped channel or bore 90 that is aligned with a channel 17 formed in the body 16. The boom arm housing 26 includes a first engagement member 94 configured to selectively and detachably couple the shuttling element 40 within the boom arm housing 26 when the shuttling element 40 is to be retained within the boom arm housing 26. As shown, the first engagement member 94 may be a flange 96 extending from an internal surface 98 of the boom arm housing 26. The bore 90 of the boom arm housing 26 has a height H3 measured from opposing internal surfaces 98 in the transverse direction T. The bore has a height H4 measured from opposing internal surfaces 98 in the transverse direction T at the location of the flange 96. The height H4 can be less than the height H3.

The boom arm housing 26 can include a single piece of material, or as shown two opposing boom arm housing portions 100 that define a gap 102 between the boom arm housing portions 100. The boom arm housing portions 100 act as leaf springs such that they are separable from each other in the lateral direction A thus widening the gap 102. However, once separated the boom arm housing portions 100 will exert a force attempting to close the gap 102 back to its original state. The use of boom arm housing portions 100 can provide tactile feedback to an operator of the bi-directional suture passing instrument 10.

Referring to FIGS. 5A and 5B the shuttling element 40 and the boom arm housing 26 are in an unlocked configuration. In the unlocked configuration the shuttling element 40 is free to translate with respect to the boom arm housing 26 along the longitudinal direction L. As shown, the width W2 of the shuttling element 40 is aligned with the height H3 and H4 of the bore 90 of the boom arm housing 26. Because the width W2 is less than both the height H3 and H4, the shuttling element 40 is free to translate within the bore 90 of the boom arm housing 26.

Referring to FIGS. 6A and 6B the shuttling element 40 and the boom arm housing 26 are in a locked configuration. In the locked configuration the shuttling element 40 is not separable from the boom arm housing 26 along the longitudinal direction L. As shown, once the third engagement member 66 is aligned with the first engagement member 94 the shuttling element 40 can be rotated such that the height H2 of the shuttling element 40 is aligned with the height H3 and the height H4 of the bore 90 of the boom arm housing 26. This rotation results in the first engagement member 94 and the third engagement member 66 being mated. As shown, the flange 96 is disposed within the recessed radial groove 68 such that the flange 96 is between the opposing retention walls 70. Because the height H2 is less than the height H3 but greater than the height H4, the shuttling element 40 is locked within the bore 90 of the boom arm housing 26 such that the shuttling element 40 and the boom arm housing 26 cannot be separated by translation of the shuttling element 40 in the longitudinal direction L. Translation of the shuttling element 40 relative to the boom arm housing 26 is blocked by the opposing retention walls 70 interfering with the flange 96.

Figure 7A:
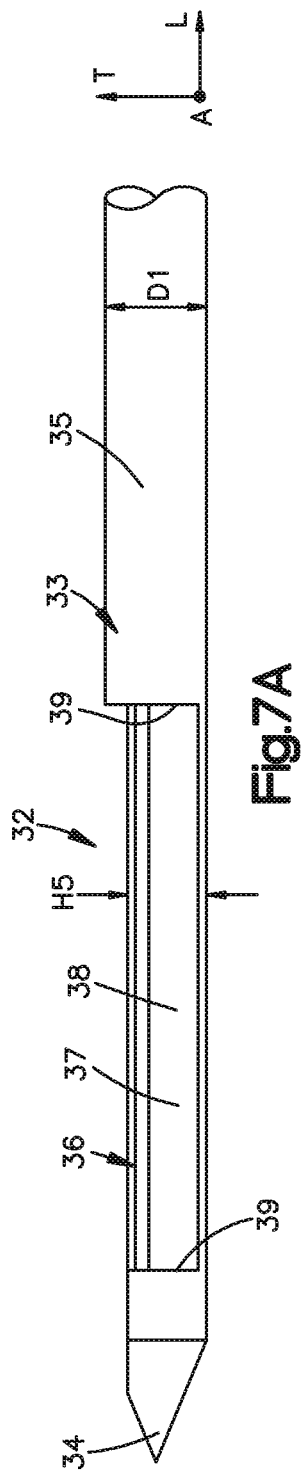
FIG. 7A is a side view of the needle illustrated in FIG. 1D.
Figure 7B:
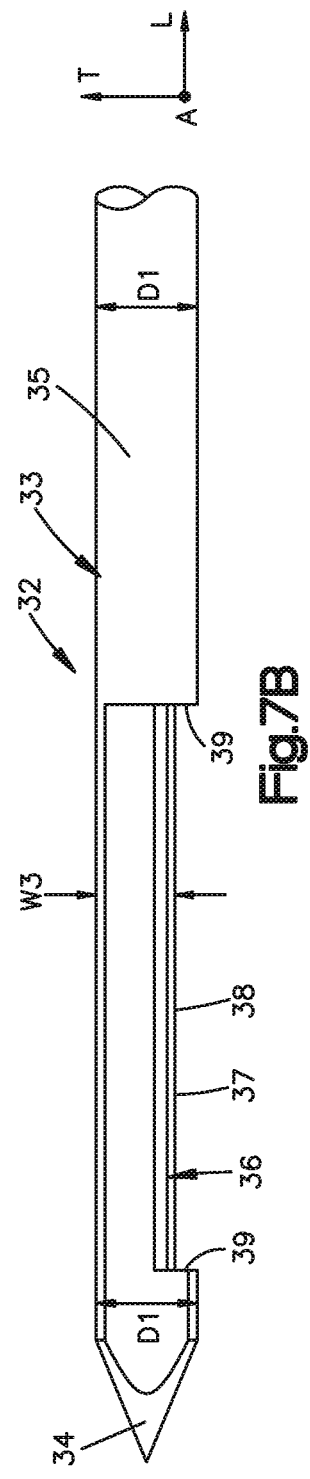
FIG. 7B is a top view of the needle illustrated in FIG. 7A.
Figure 7C:
FIG. 7C is a front view of the needle illustrated in FIG. 7A.

Referring to FIGS. 7A-7C, the needle 32 can include a body 33 with a tip 34, a shaft portion 35 and an engagement portion 36. The shaft portion 35 defines an outer dimension D1 that is sized and configured to fit and translate within the channel 17 of body 16. The engagement portion 36 is sized and configured to fit and translate within the bore 50 of the shuttling element 40 and the engagement portion 36 is also configured to selectively engage the shuttling element 40 such that the needle 32 and the shuttling element 40 become locked. The engagement portion 36 can also include a second engagement member 37. As shown the second engagement member 37 has a recessed flat 38 that is defined by opposing side walls 39. Alternatively, the second engagement member 37 could be a recess, a groove, a protrusion, a notch, a raised flat, or any other structure that is matable with a corresponding engagement member 52 of the shuttling element 40. The engagement portion 36 defines a height H5 and a width W3 that can be measured at an angular offset to each other. As shown that height H5 and the width W3 are measured perpendicular to each other, with the height H5 being measured in the transverse direction T and the width W3 being measured in the lateral direction A. As shown the width W3 extends between two sections of the shaft portion 35 with the outer dimension D1, and the outer dimension D1 as measured in the transverse direction being greater than the width W3 measured in the transverse direction. The height H5 as shown does not have a distal portion of the body 33 with an outer dimension D1 that is greater than the height H5.

Figure 8A:
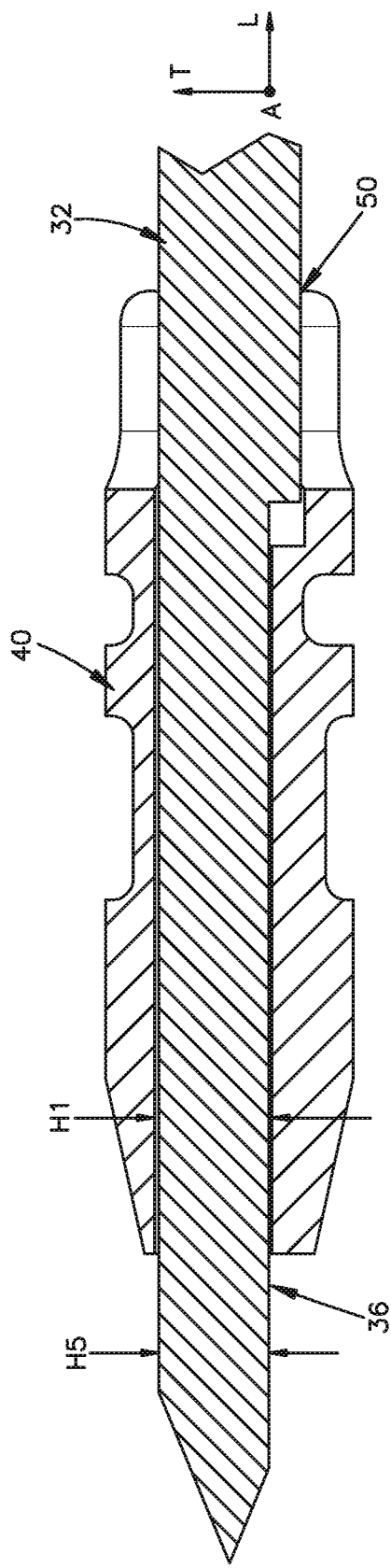
FIG. 8A is a cross-sectional view of the shuttling element and the needle illustrated in FIG. 1D, in an unlocked configuration.

Referring to FIG. 8A the shuttling element 40 and the needle 32 are in an unlocked configuration. In the unlocked configuration the needle 32 is free to translate with respect to the shuttling element 40 along the longitudinal direction L. As shown, the height H5 of the engagement portion 36 of the needle 32 is aligned with the height H1 of the bore 50 of the shuttling element 40. Because the height H5 is less than the height H1, the needle 32 is free to translate within the bore 50 of the shuttling element 40.

Figure 8B:
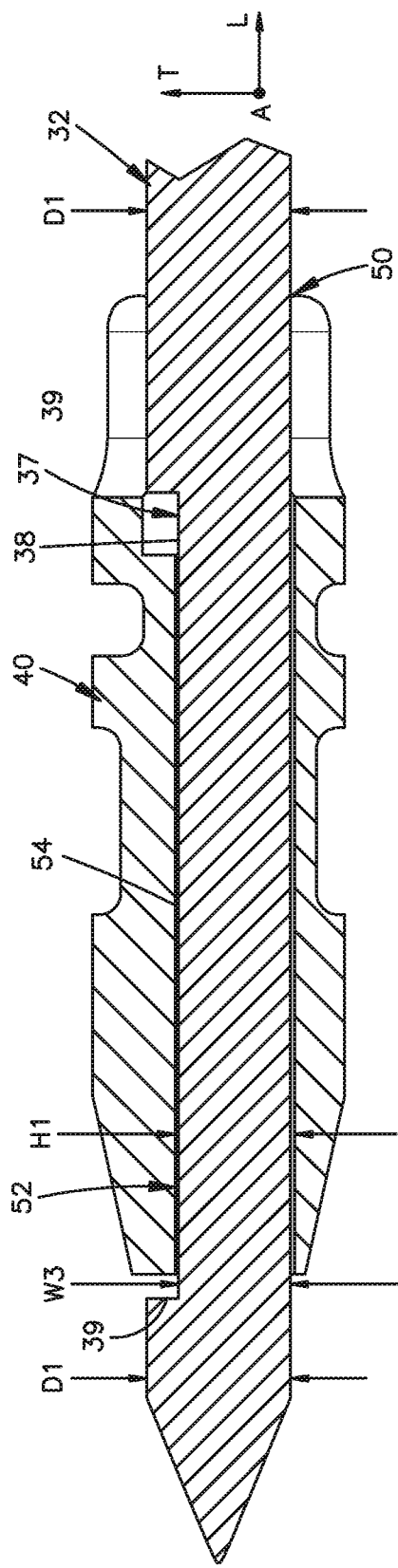
FIG. 8B is a cross-sectional view of the shuttling element and the needle illustrated in FIG. 8A, in a locked configuration.

Referring to FIG. 8B the shuttling element 40 and the needle 32 are in a locked configuration. In the locked configuration the shuttling element 40 is not separable from the needle 32 along the longitudinal direction L. As shown, once the second engagement member 37 is aligned with the fourth engagement member 52 the shuttling element 40 can be rotated with respect to the needle 32 such that the height H1 of the bore 50 of the shuttling element 40 is aligned with the width W3 of the second engagement member 37. This rotation results in the second engagement member 37 and the fourth engagement member 52 being mated. As shown, the raised flat 54 is disposed within the recessed flat 38 such that the raised flat 54 is between the opposing side walls 39. Because the height H1 is greater than the width W3 but less than the outer dimension D1, the needle 32 is locked within the bore 50 of the shuttling element 40 such that the needle 32 and the shuttling element 40 cannot be separated by translation of the needle 32 in the longitudinal direction L. Translation of the needle 32 relative to the shuttling element 40 is blocked by the opposing side walls 39 interfering with the raised flat 54.

Referring to FIGS. 9A-10, the sheath 20 includes a body 122 having a proximal portion 124, a distal portion 126 and an intermediate portion 128 extending between the proximal portion 124 and the distal portion 126. The body 122 is elongate along the longitudinal direction L and defines a bore or channel (not shown) that extends through the entire body 122 from the proximal portion 124 to the distal portion 126, the bore or channel being configured to slidably receive the needle 32. The body 122 also has an outer surface 130 that defines an outer dimension D2 such that the sheath 20 is configured to be slidably received within the channel 17 of the body 16 (as shown in FIG. 1D). Referring again to FIGS. 9A-10, the distal portion 126 can include protrusions 132 that define at least one recess 134. The protrusion 132 can be sized and configured to fit within the actuation slot 78 of the shuttling element 40 and the recess 134 can be sized and configured to receive the flange 76 of the shuttling element 40. As shown the protrusions 132 and recesses 134 can be mated with the actuation slot 78 and flange 76 such that any translation movement of the sheath such as translation or rotation will be transferred to the shuttling element 40 causing a translation or rotation of the shuttling element 40.

Referring to FIGS. 11A-11B and 12A-12B, the shuttling element 40 according to another embodiment and the needle 32 according to another embodiment each have many features similar to those described above. Only those features that are different are discussed in detail here. The fourth engagement feature 52 of the shuttling element 40 as shown includes at least one protrusion 55. The second engagement feature 37 of the needle includes a groove 160. The groove has a longitudinal portion 162 and a radial portion 164. The groove 160 is sized and configured to receive the protrusion 55 such that when the protrusion 55 is aligned with the groove 160 the needle 32 can translate with respect to the shuttling element 40 in the longitudinal direction.

Figure 13A:
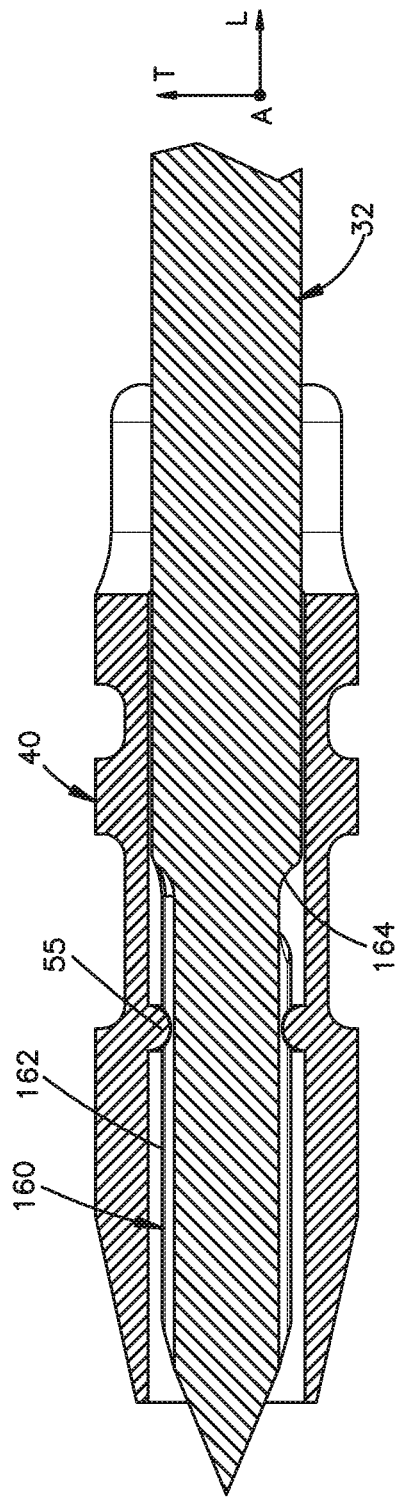
FIG. 13A is a cross sectional view of the shuttling element illustrated in FIG. 11A and the needle illustrated in FIG. 12A in an unlocked configuration.
Figure 13B:
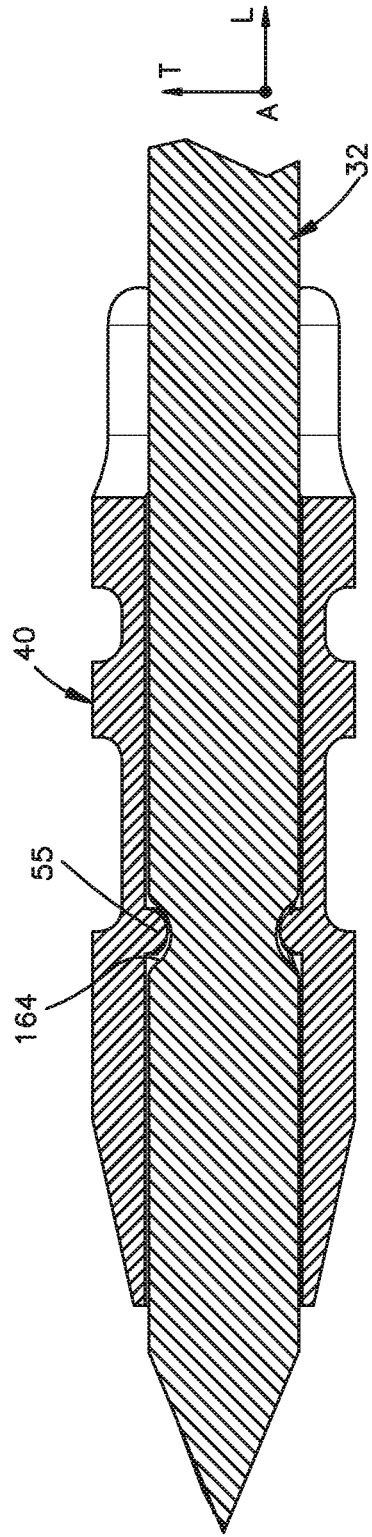
FIG. 13B is a cross sectional view of the shuttling element and the needle illustrated in FIG. 13A in a locked configuration.
Figure 15A:
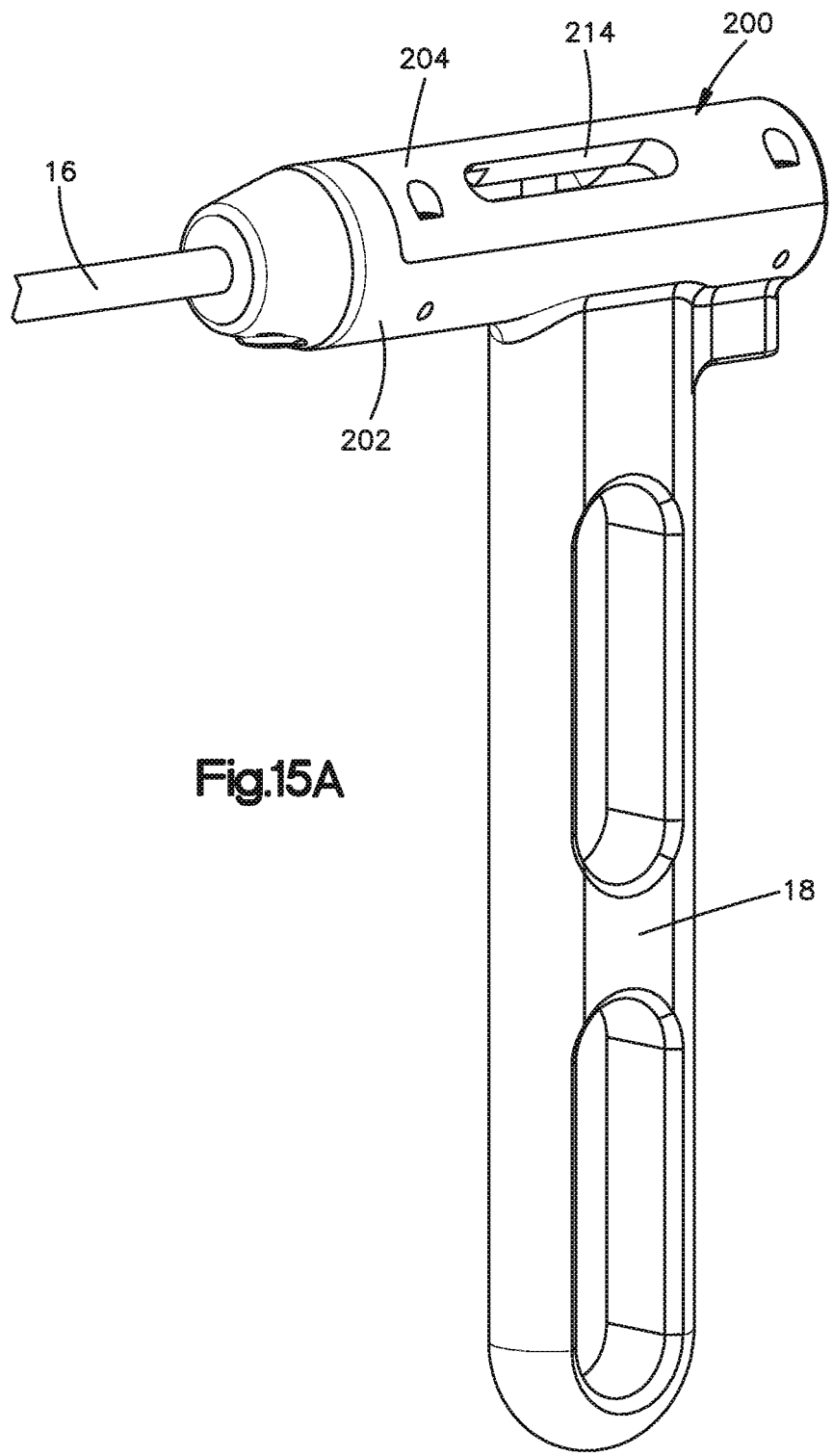
FIG. 15A is a perspective view of the handle and the body illustrated in FIG. 1A and a housing joining the handle and the body.

Referring to FIGS. 13A-13B, in use the shuttling element 40 is angularly oriented with the needle 32 such that the longitudinal portion 162 of the groove 160 is aligned with the protrusion 55. The needle 32 can then be advanced until the protrusion 55 reaches the end of the longitudinal portion 162. The shuttling element 40 can then be rotated which allows the protrusion 55 to follow the radial portion 164 of the groove 160. Once the protrusion 55 has reached the end of the radial portion 164, the needle 32 and the shuttling element 40 are locked together.

Referring to FIG. 14A, the actuator 30 includes a gripping portion 170 and a securing portion 172, the securing portion 172 being translationally and rotationally locked with respect to the gripping portion 170. The gripping portion 170 is sized and configured to be manipulated by a human hand both in translation and rotation. As shown gripping portion 170 can be a knob 174. The securing portion 170 can include a first recess 176 that is configured to receive a first set screw and a second recess 178 configured to receive a second set screw, the second recess 178 being disposed within a radial groove 180. The radial groove 180 has a length L2 measured along the longitudinal direction L. The securing portion 170 can also include a bore 182 that is configured to receive the sheath 20. Additionally, the securing portion can include a protrusion (for example a set screw 184 or other follower for a track 212 as will be discussed below in reference to FIG. 16).

Referring to FIG. 14B, a connector 230 includes a body 232 and a protrusion 234. The body 232 defines a bore 236 that is sized and configured to receive the needle 32. The needle 32 can be secured within the bore 236, for example, by a set screw inserted in a recess 238. The protrusion 234 defines an outer dimension D3.

Referring to FIG. 14C, the connector 230 is positioned within the actuator 30. As shown the outer dimension D3 of the protrusion 234 is smaller than the length L2 of the radial groove 180 such that the protrusion 234 can rotate within the radial groove 180 about the longitudinal direction L but the protrusion cannot translate within the radial groove 180 along the longitudinal direction L. This configuration allows the actuator 30, the sheath 20 and the needle 32 (not shown, positioned within the sheath 20) to be locked in respect to translation along the longitudinal direction L while the actuator 30 and the sheath 20 can rotate with respect to the needle 32 about the longitudinal direction L.

Referring to FIGS. 15A-15D, the bi-directional suture passing instrument 10 can further include a housing 200. The housing 200 joins the body 16 to the handle 18 and also can include features to limit the relative movement of the needle 32, sheath 20, and actuator 30 as will be described in greater detail below. The housing 200 can be integral with the body 16 or alternatively can be separable from the body 16. The housing 200 can include a securing member 202 and a guidance member 204. The securing member 202 of the housing 200 has a bore 206 that is configured to receive the body 16 and secure the body 16 relative to the securing member 202. A set screw can be inserted into a first recess 208 to secure the body 16 relative to the securing member 202. The securing member 202 can also include a longitudinal groove 210.

The guidance member 204 can be configured to restrict movement of the actuator 30 such that the shuttling element 40 can only be rotated when the needle 32 is in the advanced position. As shown the guidance member 204 can include a track 212 with a first longitudinal portion 214 a second longitudinal portion 216 and a lateral portion 218 extending between and joining the first longitudinal portion 214 to the second longitudinal portion 216. The track 212 is configured such that rotation of the actuator 30 is restricted unless the needle is in the advanced position.

Referring to FIG. 16, the needle 32 and the sheath 20 are each positioned within the channel 17 of the body 16 such that each of the needle 32, the sheath 20, and the body 16 extend into the housing 200. The body 16 is secured to the securing member 202 such that the body 16 and the securing member 202 cannot translate or rotate relative to one another. As shown, the body 16 and the securing member 202 can be secured by a set screw 220. The sheath 20 extends through the securing member 202 and into the bore 182. The sheath 20 is secured to the actuator 30 such that the sheath 20 and the actuator 30 cannot translate or rotate relative to one another. As shown, the sheath 20 and the actuator 30 can be secured by a set screw 222. The needle 32 extends through the securing member 202, and into the bore 182. The needle 32 is secured to the actuator 30 such that the needle 32 and the actuator 30 cannot translate relative to one another in the longitudinal direction L but they can rotate relative to one another about the longitudinal direction L. As shown, the protrusion 234 extends through the radial groove 180 of the actuator 30 and into the longitudinal groove 210 of the securing member 202. The longitudinal groove 210 is configured to receive the protrusion 234 such that the protrusion can slide within the longitudinal groove 210 in the longitudinal direction L but not rotate within the longitudinal groove 210 about the longitudinal direction L. The connector 230 and the needle 32 can be secured by a set screw 224.

Referring to FIGS. 2A-2D and 14A-16, in use the actuator 30 is positioned within the housing 200 between the securing member 202 and the guidance member 204, such that the actuator 30 is translatable and rotatable relative to the housing 200. A set screw 184 can be attached to the actuator 30 and positioned within the track 212. When the set screw 184 is positioned proximally within the first longitudinal portion 214 the needle 32 is in the retracted position, the actuator 30 can be translated in the longitudinal direction L. As the set screw 184 rides along the first longitudinal portion 214 the actuator 30, the sheath 20 and the needle 32 all translate together as the needle 32 is moved into the advanced position. The actuator 30 can then be rotated about the longitudinal direction L as the set screw 184 rides along the lateral portion 218 of the track 212. The sheath 20 rotates with the actuator 30 and while the needle 32 does not rotate due to interference between the protrusion 234 and the longitudinal groove 210. The rotation of the sheath 20 causes the shuttling element 40 to rotate and both unlock from the boom arm housing 26 and lock to the needle 32. The actuator 30 can then be moved proximally as the set screw 184 rides along the second longitudinal portion 216 until the needle 32 is once again in the retracted position.

Referring to FIGS. 17A and 17B, the shuttling element 40 according to another embodiment has many features similar to those described above. Only those features that are different are discussed in detail here. The third engagement member 66 of the shuttling element 40 as shown includes a first flange 266 and a second flange 268 and a gap 270 extending between the first flange 266 and the second flange 268. The first flange 266 and the second flange 268 each extend from the outer surface 56 of the shuttling element 40 in the transverse direction T defining a height H6. The second flange 268 can include an attachment member 267 configured to securing the suture 4 to the shuttling element 40. As shown, the attachment member 267 can be a bore 269.

Referring to FIG. 18, the boom arm housing 26 according to another embodiment has many features similar to those described above. Only those features that are different are discussed in detail here. The first engagement member 94 can include a first primary locking mechanism 294. The first primary locking mechanism 294 is configured to be received within the gap 270 such that translation of the shuttling element 40 along the longitudinal direction is blocked by interference between the first flange 266 and the first primary locking mechanism 294 in one direction and the second flange 268 and the first primary locking mechanism 294 in the other direction. A second primary locking mechanism 296 can be included to define a gap 298 between the first primary locking mechanism 294 and second primary locking mechanism 296, the gap 298 being configured to receive and secure the first flange 266 once they are in the locked configuration.

Referring to FIG. 19A, the shuttling element 40 and the boom arm housing 26 are in an unlocked configuration. In the unlocked configuration the shuttling element 40 is free to translate with respect to the boom arm housing 26 along the longitudinal direction L. As shown, the first flange 266 and the second flange 268 (not shown) of the shuttling element 40 are aligned with the bore 90 of the boom arm housing 26 such that the outer dimension D4 of the bore is greater than the height H6 of the shuttling element 40 thus allowing the shuttling element 40 to translate within the bore 90 of the boom arm housing 26.

Referring to FIGS. 18 and 19B, the shuttling element 40 and the boom arm housing 26 are in a locked configuration. In the locked configuration the shuttling element 40 is not separable from the boom arm housing 26 along the longitudinal direction L. As shown, once the first flange 266 is aligned with the gap 298 the shuttling element 40 can be rotated such that the first flange 266 is received and secured within the gap 298 of the boom arm housing 26. This rotation results in the first engagement member 94 and the third engagement member 66 being mated.

Referring to FIGS. 20A and 20B, the bi-directional suture passing instrument 10 can include a secondary locking mechanism 300. The secondary locking mechanism 300 is configured to provide additional protection against undesired rotation of the shuttling element 40 which can lead to premature locking or unlocking of the shuttling element 40 and the boom arm housing 26. As shown, the secondary locking mechanism 300 can be a shaft member 302. The shaft member 302 can be in a locked position or an unlocked position. In the locked position the shaft member 302 is disposed within the path of rotation of the first flange 266 and in the unlocked position the shaft member 302 is removed from the path of rotation of the first flange 266. The shaft member 302 can be biased to the locked position or alternatively biased to the unlocked position or alternatively still not biased to either the locked or unlocked position.

Referring to FIGS. 20A-20C, the secondary locking mechanism 300 can be locked to the sheath 20 such that as the sheath 20 and the needle 32 translate in the longitudinal direction L within to the body 16, the secondary locking mechanism 300 also translates in the longitudinal direction L. As shown, the secondary locking mechanism 300 can include tabs 304 that are configured to be received within a recess 306 of the sheath 20. As sheath 20 translates distally, a front surface 308 of the shaft member 302 comes into contact with the second primary locking mechanism 296. The front surface 308 can be configured such that further translation of the sheath 20 causes the front surface 308 to ride along the second primary locking mechanism 296 such that the shaft member 302 moving from the locked position to the unlocked position. The secondary locking mechanism 300 can also include a locking member 310 configured to secure the secondary locking mechanism 300 in the locked position within the boom arm 22. As shown the locking member can be a pin or shaft member that blocks translation of the secondary locking mechanism 300 in the longitudinal direction L.

Referring to FIGS. 1A-20C, a bi-directional suture passing instrument 10 configured to approximate a soft tissue defect 2 can include: a body 16 that defines a channel 17, and a boom arm 22 that extends from the body 16, the boom arm 22 having a boom arm housing 26 that is spaced from the body 16, the boom arm 22 also having an offset arm portion 24 that extends between the body 16 and the boom arm housing 26, such that a tissue-receiving gap 28 extends between the boom arm housing 26 and the body 16; a needle 32 reciprocally translatable within the channel 17 between an advanced position in which the needle 32 extends at least into the boom arm housing 26, and a retracted position in which the needle 32 is retracted from the boom arm housing 26; and a shuttling element 40 configured to carry a suture 4 across the tissue-receiving gap 28; wherein movement of the shuttling element 40 relative to both the boom arm housing 26 and the needle 32 causes the shuttling element 40 to 1) both lock to the boom arm housing 26 and unlock from the needle 32, or 2) both unlock from the boom arm housing 26 and lock to the needle 32.

Alternatively, a bi-directional suture passing instrument 10 configured to approximate soft tissue defects 2, the suture passing instrument 10 can include: a body 16 that defines a channel 17, the channel 17 extending along a longitudinal axis 1; a boom arm 22 that extends from the body 16, the boom arm 22 having a boom arm housing 26 that is spaced from the body 16, the boom arm 22 also having an offset arm portion 24 that extends between the body 16 and the boom arm housing 26, such that a tissue-receiving gap 28 extends between the boom arm housing 26 and the body 16; a needle 32 reciprocally translatable within the channel 17 between an advanced position in which the needle 32 extends at least into the boom arm housing 26, and a retracted position in which the needle 32 is retracted from the boom arm housing 26; and a shuttling element 40 configured to carry a suture 4 across the tissue-receiving gap 28; wherein a single rotational movement of the shuttling element 40 relative to both the boom arm housing 26 and the needle 32 causes the shuttling element 40 to 1) both lock to the boom arm housing 26 and unlock from the needle 32, or 2) both unlock from the boom arm housing 26 and lock to the needle 32.

In another alternative, a bi-directional suture passing instrument 10 can include: a body 16 that defines a channel 17, and a boom arm 22 extending from the body 16, the boom arm 22 including: 1) a boom arm housing 26 that is spaced from the body 16, the boom arm housing 26 having an interior surface 98 defining a bore 90, the interior surface 98 having a first engagement member 94; and 2) an offset arm portion 24 extending between the body 16 and the boom arm housing 26 such that a tissue-receiving gap 28 is disposed between the boom arm housing 26 and the body 16; a needle 32 reciprocally translatable within the channel 16 between an advanced position in which the needle 32 extends at least into the boom arm housing 26, and a retracted position in which the needle 32 is retracted from the boom arm housing 26, the needle 32 defining a second engagement member 37; and a shuttling element 40 configured to carry a suture 4 across the tissue-receiving gap 28, the shuttling element 40 having: an outer surface 56 including a third engagement member 66; and an inner surface 48 defining an inner bore 50 and including a fourth engagement member 52; wherein in a first angular orientation the first and third engagement members 94, 66 are mated such that the boom arm housing 26 and the shuttling element 40 can be separated only by rotation of the shuttling element 40 relative to the boom arm housing 26, and in a second angular orientation the second and fourth engagement members 37, 52 are mated such that the needle 32 and the shuttling element 40 can be separated only by rotation of the shuttling element 40 relative to the needle 32.

It will be appreciated by those skilled in the art that changes could be made to the embodiments described above without departing from the broad inventive concept thereof. It is understood, therefore, that this disclosure is not limited to the particular embodiments disclosed, but it is intended to cover modifications within the spirit and scope of the present disclosure as defined by the claims.

What is claimed:

1. A bi-directional suture passing instrument configured to approximate soft tissue defects, the suture passing instrument comprising:
   a body that defines a channel, and a boom arm that extends from the body, the boom arm having a boom arm housing that is spaced from the body, the boom arm also having an offset arm portion that extends between the body and the boom arm housing, such that a tissue-receiving gap extends between the boom arm housing and the body;
   a needle reciprocally translatable along a direction of translation within the channel between an advanced position in which the needle extends at least into the boom arm housing, and a retracted position in which the needle is retracted from the boom arm housing; and
   a shuttling element configured to carry a suture across the tissue-receiving gap;
   wherein movement of the shuttling element relative to the boom arm housing that is different than movement along the direction of translation causes the shuttling element to 1) both lock to the boom arm housing and unlock from the needle, or 2) both unlock from the boom arm housing and lock to the needle.

2. The bi-directional suture passing instrument of claim 1, wherein movement of the shuttling element relative to the needle causes the shuttling element to 1) both lock to the boom arm housing and unlock from the needle, or 2) both unlock from the boom arm housing and lock to the needle, and wherein the movement of the shuttling element relative to the boom arm housing and the movement of the shuttling element relative to the needle are the same movement.

3. The bi-directional suture passing instrument of claim 2, wherein movement of the shuttling element in a first direction relative to both the boom arm housing and the needle causes the shuttling element to both lock to the boom arm housing and unlock from the needle, and movement of the shuttling element in a second direction different than the first direction relative to both the boom arm housing and the needle causes the shuttling element to both lock to the needle and unlock from the boom arm housing.

4. The bi-directional suture passing instrument of claim 3, wherein the movement of the shuttling element in the first direction is opposite the movement of the shuttling element in the second direction.

5. The bi-directional suture passing instrument of claim 3, wherein the boom arm housing has a first engagement member, the needle has a second engagement member, and the shuttling element has third and fourth engagement members, and movement in the first direction causes the first and third engagement members to engage such that the boom arm housing and the shuttling element are locked and the second and fourth engagement members to disengage such that the needle and the shuttling element are unlocked.

6. The bi-directional suture passing instrument of claim 5, wherein movement in the second direction causes the second and fourth engagement members to engage such that the needle and the shuttling element are locked and the first and third engagement members to disengage such that the boom arm housing and the shuttling element are unlocked.

7. The bi-directional suture passing instrument of claim 6, wherein when the boom arm housing and the shuttling element are locked the boom arm housing and the shuttling element can be separated only by rotation of the shuttling element relative to the boom arm housing and when the needle and the shuttling element are locked the needle and the shuttling element can be separated only by rotation of the shuttling element relative to the needle.

8. The bi-directional suture passing instrument of claim 7, wherein when the boom arm housing and the shuttling element are unlocked the boom arm housing and the shuttling element are separable by translation of the shuttling element relative to the boom arm housing and when the needle and the shuttling element are unlocked the needle and the shuttling element are separable by translation of the needle relative to the shuttling element.

9. The bi-directional suture passing instrument of claim 8, further comprising:
   the boom arm housing having an inner surface that defines a bore extending into the boom arm housing and the inner surface of the boom arm housing comprises the first engagement member;
   the needle having an outer surface that comprises the second engagement member; and
   the shuttling element having an outer surface that comprises the third engagement member and the shuttling element having an inner surface defining an inner bore, the inner surface comprising the fourth engagement member.

10. The bi-directional suture passing instrument of claim 9, wherein the first and third engagement members comprise a first protrusion and a corresponding first groove.

11. The bi-directional suture passing instrument of claim 9, wherein the second and fourth engagement members comprise a second protrusion and a corresponding second groove.

12. The bi-directional suture passing instrument of claim 11, wherein the second protrusion and the corresponding second groove comprise a raised flat and a recessed flat, respectively.

13. The bi-directional suture passing instrument of claim 2, wherein the movement of the shuttling element is a rotation.

14. The bi-directional suture passing instrument of claim 13, wherein the channel is elongate along a longitudinal axis, and the rotation of the shuttling element is about the longitudinal axis.

15. The bi-directional suture passing instrument of claim 14, further comprising at least one actuator configured to (i) translate the needle within the channel between the advanced position and the retracted position and (ii) rotate the shuttling element about the longitudinal axis.

16. The bi-directional suture passing instrument of claim 15, wherein the needle is rotationally locked with respect to the body.

17. The bi-directional suture passing instrument of claim 15, wherein the body further comprises a guidance member that restricts movement of the actuator such that the shuttling element can only be rotated when the needle is in the advanced position.

18. The bi-directional suture passing instrument of claim 17, wherein, the shuttling element is always positively engaged to at least one of the needle or boom arm housing.

19. The bi-directional suture passing instrument of claim 17, wherein the guidance member comprises a track and the actuator comprises a follower configured to ride along the track, the track is configured such that rotation of the actuator is restricted unless the needle is in the advanced position.

20. The bi-directional suture passing instrument of claim 19, wherein the actuator comprises:
a knob extending at least partially from the body; and
a sheath positioned at least partially within the channel and coupled to the knob such that (i) translation of the knob along the longitudinal axis results in translation of the sheath along the longitudinal axis and (ii) rotation of the knob about the longitudinal axis results in rotation of the sheath about the longitudinal axis;
wherein the sheath is configured to selectively engage the shuttling element such that when the shuttling element and the sheath are engaged, rotation of the knob will cause the shuttling element to rotate about the longitudinal axis.

21. A bi-directional suture passing instrument configured to approximate soft tissue defects, the suture passing instrument comprising:
a body that defines a channel, the channel extending along a longitudinal axis;
a boom arm that extends from the body, the boom arm having a boom arm housing that is spaced from the body, the boom arm also having an offset arm portion that extends between the body and the boom arm housing, such that a tissue-receiving gap extends between the boom arm housing and the body;
a needle reciprocally translatable within the channel between an advanced position in which the needle extends at least into the boom arm housing, and a retracted position in which the needle is retracted from the boom arm housing; and
a shuttling element configured to carry a suture across the tissue-receiving gap;
wherein a single rotational movement of the shuttling element relative to both the boom arm housing and the needle causes the shuttling element to 1) both lock to the boom arm housing and unlock from the needle, or 2) both unlock from the boom arm housing and lock to the needle.

22. The bi-directional suture passing instrument of claim 21, further comprising a guidance member connected to the body such that the guidance member allows rotation of the shuttling element only when the needle is in the advanced position.

23. The bi-directional suture passing instrument of claim 22, wherein the guidance member comprises a track and the actuator comprises a follower configured to ride along the track, and the track is configured such that rotation of the actuator is restricted unless the needle is in the advanced position.

24. The bi-directional suture passing instrument of claim 22, further comprising at least one actuator configured to (i) translate the needle within the channel between the advanced position and the retracted position and (ii) rotate the shuttling element about the longitudinal axis.

25. The bi-directional suture passing instrument of claim 24, wherein the needle is rotationally locked with respect to the body.

26. The bi-directional suture passing instrument of claim 24, wherein, the shuttling element is always positively engaged to at least one of the needle or boom arm housing.

27. The bi-directional suture passing instrument of claim 24, wherein the actuator comprises:
a knob extending at least partially from the body; and
a sheath positioned at least partially within the channel and coupled to the knob such that (i) translation of the knob along the longitudinal axis results in translation of the sheath along the longitudinal axis and (ii) rotation of the knob about the longitudinal axis results in rotation of the sheath about the longitudinal axis;
wherein the sheath is configured to selectively engage the shuttling element such that when the shuttling element and the sheath are engaged, rotation of the knob will cause the rotational movement of the shuttling element.

28. The bi-directional suture passing instrument of claim 22, wherein when the boom arm housing and the shuttling element are locked the boom arm housing and the shuttling element can be separated only by rotation of the shuttling element relative to the boom arm housing and when the needle and the shuttling element are locked the needle and the shuttling element can be separated only by rotation of the shuttling element relative to the needle.

29. The bi-directional suture passing instrument of claim 28, wherein when the boom arm housing and the shuttling element are unlocked the boom arm housing and the shuttling element are separable by translation of the shuttling element relative to the boom arm housing and when the needle and the shuttling element are unlocked the needle and the shuttling element are separable by translation of the needle relative to the shuttling element.

30. The bi-directional suture passing instrument of claim 21, wherein the boom arm housing has a first engagement member, the needle has a second engagement member, and the shuttling element has third and fourth engagement members, and the rotational movement causes the first and third engagement members to engage such that the boom arm housing and the shuttling element are locked and the second and fourth engagement members to disengage such that the needle and the shuttling element are unlocked.

31. The bi-directional suture passing instrument of claim 30, wherein the rotational movement causes the second and fourth engagement members to engage such that the needle and the shuttling element are locked and the first and third engagement members to disengage such that the boom arm housing and the shuttling element are unlocked.

32. The bi-directional suture passing instrument of claim 31, wherein the rotational movement that causes the first and third engagement members to engage is in a first direction and the rotational movement that causes the second and fourth engagement members to engage is in a second direction opposite the first direction.

33. The bi-directional suture passing instrument of claim 31, wherein when the boom arm housing and the shuttling element are locked the boom arm housing and the shuttling element can be separated only by rotation of the shuttling element relative to the boom arm housing and when the needle and the shuttling element are locked the needle and the shuttling element can be separated only by rotation of the shuttling element relative to the needle.

34. The bi-directional suture passing instrument of claim 33, wherein when the boom arm housing and the shuttling element are unlocked the boom arm housing and the shuttling element are separable by translation of the shuttling element relative to the boom arm housing and when the needle and the shuttling element are unlocked the needle and the shuttling element are separable by translation of the needle relative to the shuttling element.

35. The bi-directional suture passing instrument of claim 34, further comprising:
the boom arm housing having an inner surface that defines a bore extending into the boom arm housing and the boom arm housing inner surface comprises the first engagement member;
the needle having an outer surface that comprises the second engagement member; and
the shuttling element having an outer surface that comprises the third engagement member and the shuttling element having an inner surface defining an inner bore, the inner surface comprising the fourth engagement member.

36. The bi-directional suture passing instrument of claim 35, wherein the first and third engagement members comprise a first protrusion and a corresponding first groove.

37. The bi-directional suture passing instrument of claim 35, wherein the second and fourth engagement members comprise a second protrusion and a corresponding second groove.

38. The bi-directional suture passing instrument of claim 37, wherein the second protrusion and the corresponding second groove comprise a raised flat and a recessed flat, respectively.

39. A bi-directional suture passing instrument comprising:
a body that defines a channel, and a boom arm extending from the body, the boom arm including:
a boom arm housing that is spaced from the body, the boom arm housing having an interior surface defining a bore, the interior surface having a first engagement member; and
an offset arm portion extending between the body and the boom arm housing such that a tissue-receiving gap is disposed between the boom arm housing and the body;
a needle reciprocally translatable within the channel between an advanced position in which the needle extends at least into the boom arm housing, and a retracted position in which the needle is retracted from the boom arm housing, the needle defining a second engagement member; and
a shuttling element configured to carry a suture across the tissue-receiving gap, the shuttling element having:
an outer surface including a third engagement member; and
an inner surface defining an inner bore and including a fourth engagement member;
wherein in a first angular orientation the first and third engagement members are mated such that the boom arm housing and the shuttling element can be separated only by rotation of the shuttling element relative to the boom arm housing, and in a second angular orientation the second and fourth engagement members are mated such that the needle and the shuttling element can be separated only by rotation of the shuttling element relative to the needle.

40. The bi-directional suture passing instrument of claim 39, wherein in the first angular orientation the shuttling element is translatable into the bore of the boom arm housing.

41. The bi-directional suture passing instrument of claim 40, wherein in the second angular orientation the needle is translatable into the inner bore of the shuttling element.

42. The bi-directional suture passing instrument of claim 41, wherein the first and third engagement members comprise a first protrusion and a corresponding first groove.

43. The bi-directional suture passing instrument of claim 41, wherein the second and fourth engagement members comprise a second protrusion and a corresponding second groove.

44. The bi-directional suture passing instrument of claim 43, wherein the second protrusion and the corresponding second groove comprise a raised flat and a recessed flat, respectively.

45. A bi-directional suture passing instrument configured to approximate soft tissue defects, the suture passing instrument comprising:
a body that defines a channel, and a boom arm that extends from the body, the boom arm having a boom arm housing that is spaced from the body, the boom arm also having an offset arm portion that extends between the body and the boom arm housing, such that a tissue-receiving gap extends between the boom arm housing and the body;
a needle reciprocally translatable within the channel between an advanced position in which the needle extends at least into the boom arm housing, and a retracted position in which the needle is retracted from the boom arm housing; and
a shuttling element configured to carry a suture across the tissue-receiving gap;
wherein rotation of the shuttling element relative to the needle causes the shuttling element to 1) both lock to the boom arm housing and unlock from the needle, or 2) both unlock from the boom arm housing and lock to the needle.

46. The bi-directional suture passing instrument of claim 45, wherein rotation of the shuttling element in a first direction relative to the needle causes the shuttling element to both lock to the boom arm housing and unlock from the needle, and rotation of the shuttling element in a second direction different than the first direction relative to the needle causes the shuttling element to both lock to the needle and unlock from the boom arm housing.

47. The bi-directional suture passing instrument of claim 45, wherein the channel is elongate along a longitudinal axis, and the rotation of the shuttling element is about the longitudinal axis.

* * * * *